US007300791B2

(12) United States Patent
Ferrara et al.

(10) Patent No.: US 7,300,791 B2
(45) Date of Patent: *Nov. 27, 2007

(54) PRODUCTION OF VASCULAR ENDOTHELIAL CELL GROWTH FACTOR AND DNA ENCODING SAME

(75) Inventors: Napoleone Ferrara, San Francisco, CA (US); David Wai-Hung Leung, Mercer Island, WA (US)

(73) Assignee: Genentech, Inc., South San Francisco, CA (US)

( * ) Notice: Subject to any disclaimer, the term of this patent is extended or adjusted under 35 U.S.C. 154(b) by 763 days.

This patent is subject to a terminal disclaimer.

(21) Appl. No.: 10/150,046

(22) Filed: May 17, 2002

(65) Prior Publication Data

US 2003/0100072 A1    May 29, 2003

Related U.S. Application Data

(60) Continuation of application No. 08/978,791, filed on Nov. 26, 1997, now abandoned, which is a continuation of application No. 08/749,710, filed on Nov. 15, 1996, now abandoned, which is a continuation of application No. 08/459,385, filed on Jun. 2, 1995, now abandoned, which is a division of application No. 08/306,213, filed on Sep. 14, 1994, now abandoned, which is a continuation of application No. 08/047,756, filed on Apr. 15, 1993, now abandoned, which is a continuation of application No. 07/351,117, filed on May 12, 1989, now abandoned.

(51) Int. Cl.
*C12N 5/00* (2006.01)
*C12N 15/00* (2006.01)
*C12N 15/12* (2006.01)
*C12N 15/18* (2006.01)
*C12Q 1/68* (2006.01)

(52) U.S. Cl. .................. 435/325; 536/23.5; 435/6; 435/320.1; 435/252.3

(58) Field of Classification Search .................... None
See application file for complete search history.

(56) References Cited

U.S. PATENT DOCUMENTS

| 4,444,760 | A | 4/1984 | Thomas, Jr. |
| 4,456,550 | A | 6/1984 | Dvorak et al. |
| 4,721,672 | A | 1/1988 | Vallee et al. |
| 4,863,899 | A | 9/1989 | Todaro |
| 5,008,196 | A | 4/1991 | Connolly et al. |
| 5,073,492 | A | 12/1991 | Chen et al. |
| 5,194,596 | A | 3/1993 | Tischer et al. |
| 5,219,739 | A | 6/1993 | Tischer et al. |
| 5,227,302 | A | 7/1993 | Heldin et al. |
| 5,240,848 | A | 8/1993 | Keck et al. |
| 5,332,671 | A | 7/1994 | Ferrara et al. |
| 6,899,882 | B1 | 5/2005 | Ferrara et al. |
| 2002/0137900 | A1 | 9/2002 | Ferrara et al. |
| 2003/0092617 | A1 | 5/2003 | Ferrara et al. |
| 2003/0114374 | A1 | 6/2003 | Ferrara et al. |
| 2006/0025577 | A1 | 2/2006 | Ferrara et al. |

FOREIGN PATENT DOCUMENTS

| EP | 399816 | 11/1990 |
| EP | 370989 B1 | 9/1996 |
| WO | WO 90/11084 | 10/1990 |

OTHER PUBLICATIONS

Edge et al., "Total Synthesis of a Human Leukocyte Inferferon Gene" *Nature* 292:756-762 (1981).
Hunkapiller et al, "A microchemical facility for the analysis and synthesis of genes and proteins" *Nature* 310:105-111 (1984).
Abraham et al., "Human basic fibroblast growth factor: nucleotide sequence and genomic organization" *EMBO Journal* 5(10) : 2523-2528 (1986).
Beck et al., "Isolation and characterization of a vascular permeability factor from stimulated U937 cells" *J. Leukocyte Biol.* 42 (5) : 568, 1987.
Bruce et al., "Vascular permeability induced by protein product of malignant brain tumors: inhibition by dexamethasone" *J. Neurosurg.* 67:880-884 (1987).
Burgess et al., "Multiple forms of endothelial cell growth factor" *Journal of Biological Chemistry* 260:11389-11392 (1985).
Burgess et al., "Structural evidence that endothelial cell growth factor β is the precursor of both endothelial cell growth factor α and acidic fibroblast growth factor" *Proc. Natl. Acad. Sci. USA* 83:7216-7220 (1986).
Conn et al., "Amino acid and CDNA sequences of a vascular endothelial cell mitogen that is homologous to platelet-derived growth factor" *Proc. Natl. Acad. Sci. USA* 87 : 2628-2632 (1990).
Conn et al., "Purification of a glycoprotein vascular endothelial cell mitogen from a rat glioma-derived cell line" *Proc. Natl. Acad. Sci. USA* 87 : 1323-1327 (1990).
Connolly et al., "Human Vascular Permeability Factor" *Journal of Biological Chemistry* 264 (33) : 20017-20024 (1989).
Connolly et al., "Tumor vascular permeability factor stimulates endothelial cell growth and angiogenesis" *J. Clin. Invest.* 84 : 1470-1478 (1989).
Criscuolo et al., "Further characterization of malignant glioma-derived vascular permeability factor" *J. Neurosurg.* 69 : 254-262 (1988).
de Vries et al., "The fms-like tyrosine kinase, a receptor for vascular endothelial growth factor" *Science* 255 : 989-991 (1992).
Derynck et al., "Human transforming growth factor-α: Precursor structure and expression in E. coli" *Cell* 38 : 287-297 (1984).
Edge et al., "Deglycosylation of glycoproteins by trifluoromethanesulfonic acid" *Analytical Biochemstry* 118 : 131-137 (1981).

(Continued)

*Primary Examiner*—Marianne P. Allen

(57) ABSTRACT

DNA isolates coding for a vascular endothelial cell growth factor may be used to produce the protein via recombinant expression systems. Such protein is useful therapeutically to treat conditions in which a selective action on the vascular endothelial cells, in the absence of excessive connective tissue proliferation, is desirable.

6 Claims, 12 Drawing Sheets

OTHER PUBLICATIONS

Ferrara and Henzel, "Pituitary Follicular Cells Secrete a Novel Heparin-binding Growth Factor Specific for Vascular Endothelial Cells" *Biochem. & Biophys. Res. Comm.* 161(2) : 851-858 (1989).

Ferrara et al., "Pituitary follicular cells produce basic fibroblast growth factor" *Proc. Natl. Acad. Sci. USA* 84 : 5773-5777 (1987).

Ferrara et al., "The vascular endothelial growth factor family of polypeptides" *J. Cell. Biochem.* 47 : 211-218 (1991).

Finch et al., "Human KGF is FGF-related with properties of a paracrine effector of epithelial cell growth" *Science* 245:752-755 (1989).

Folkman and Klagsbrun, "Angiogenic factors" *Science* 235:442-447 (1987).

Gimenez-Gallego et al., "Brain-derived acidic fibroblast growth factor: Complete amino acid sequence and homologies" *Science* 230 : 1385-1388 (1985).

Gospodarowicz et al., "Isolation and characterization of a vascular endothelial cell mitogen produced by pituitary-derived folliculo stellate cells" *Proc. Natl. Acad. Sci. USA* 86 : 7311-7315 (1989).

Harper et al., "Human Class 1 Heparin-Binding Growth Factor: Structure and Homology to Bovine Acidic Brain Fibroblast Growth Factor" *Biochemistry* 25:4097-4103 (1986).

Ishikawa et al., "Identification of Angiogenic Activity and the Cloning and Expression of Platelet-Derived Endothelial Cell Growth Factor." *Nature.* 338:557-562 (1989).

Jaye et al., "Human Endothelial Cell Growth Factor : Cloning, Nucleotide Sequence, and Chromosome Localization" *Science* 233 :541-545 (Aug. 1, 1986).

Kaufman et al., "Expression and Amplification of DNA Introduced into Mammalian Cells" *Gene Amplification*, Cold Spring Harbor Laboratory pp. 245-250 (1982).

Keck et al., "Vascular Permeability Factor, An Endothelial Cell Mitogen Related to PDGF" *Science* 246 : 1309-1312 (1989).

Leung et al., "Vascular Endothelial Growth Factor is a Secreted Angiogenic Mitogen" *Science* 246 : 1306-1309 (1989).

Ling et al., "Isolation and partial characterization of a Mr 32, 000 protein with inhibin activity from procine follicular fluid" *Proc. Natl. Acad. Sci. USA* 82 : 7217-7221 (1985).

Marquardt et al., "Rat transforming growth factor type 1: Structure and Relation to epidermal growth factor" *Science* 223 : 1079-1082 (1984).

Ploket et al., "Isolation and characterization of a newly identified endothelial cell mitogen produced by AtT-20 cells" *EMBO Journal* 8 : 3801-3806 (1989).

Rademacher et al., "Glycobiology" *Ann. Rev. Biochem.* 57 : 785-838 (1988).

Reidhaar-Olson et al., "Combinatorial Cassette Mutagenesis as a Probe of the Information Content of Protein Sequences" *Science* 241 : 53-57 (Jul. 1, 1988).

Robertson et al., "The Isolation of Polypeptides With FSH Suppressing Activity From Bovine Follicular Fluid Which Are Structurally Different to Inhibin" *Biochem. and Biophysical Res. Comm.* 149 (2) : 744-749 (Dec. 16, 1987).

Rubin et al., "Purification and characterization of a newly identified growth factor specific for epithalial cells" *Proc. Natl. Acad. Sci. USA* 86:802-806 (1989).

Senger et al., "A highly conserved vascular permeability factor secreted by a variety of human and rodent tumor cell lines" *Cancer Research* 46:5629-5632 (1986).

Senger et al., "Purification and NH2-terminal amino acid sequences of guinea pig tumor-secreted vascular permeability factor" *Cancer Research* 50:1774-1778 (1990).

Senger et al., "Tumor cells secrete a vascular permeability factor that promotes accumulation of ascites fluid" *Science* 219:983-985 (1983).

Shimasaki et al., "Porcine Follistatin Gene Structure Supports Two Forms of Mature Follistatin Produced by Alternative Splicing" *Biochem & Biophys, Res. Comm.* 152:717-723 (1988).

Sojar et al., "A Chemical Method for the Deglycosylation of Proteins" *Archives of Biochemistry & Biophysics* 259 (1) :52-57 (1987).

Table of Contents *J. Clin. Invest.* 84 (1989).

Tischer et al., "Vascular endothelial Growth Factor: A New Member of the Platelet-Derived Growth Factor Gene Family." *Biochem. & Biophys. Res. Comm.* 165 : 1198-1206 (1989).

Ueno et al., "Vascular and Partial Characterization of Follistation: A Single-Chain Mr 35,000 Monomeric Protein that Inhibits the Release of Follicle-Stimulating Hormone" *Proc. Natl. Acad. Sci. USA* 84 : 8282-8286 (1987).

Vallette et al., "Construction of Mutant and Chimeric Genes Using the Polymerase Chain Reaction" *Nucleic Acids Research* 17(2) : 723-733 (1989).

Wang et al., "Cloning of the Gene Coding For Human Class 1 Heparin-Binding Growth Factor and Its Expression in Fetal Tissues" *Molecular & Cellular Biology* 9 (6) : 238-2395 (Jun. 1989).

Winkles et al., "Human vascular smooth muscle cells both express and respond to heparin-binding growth factor I" *Proc. Natl. Acad. Sci. USA* 84 : 7124-7128 (1987).

Wong et al., "Human GM-CSF: Molecular Cloning of the Complementary DNA and Purification of the Natural and Recombinant Proteins" *Science* 228 : 810-815 (May 17, 1985).

Yang et al., "Human IL-3 (Multi-CSF) : Identification by Expression Cloning of a Novel Hematopoietic Growth Factor Related to Murine IL-3" *Cell* 47: 3-10 (Oct. 10, 1986).

Fig. 1.

probe 5"-CCTATGGCTGAAGCGGCCAGAAGCCTCACCGAAGTTGGTGAAGTTCATGGACCTGTATCA
          **  ***  ***********  ***** ****  **
cDNA  5'-CCCATGGCAGAAGGAGGCAGAAACCCCACGAAGTGGTGAAGTTCATGGATGTCTACCA

FIG.2

SEQUENCE LISTING

<160> NUMBER OF SEQ ID NOS: 13

<210> SEQ ID NO 1
<211> LENGTH: 59

```
<212> TYPE: DNA
<213> ORGANISM: Artificial sequence
<220> FEATURE:
<223> OTHER INFORMATION: synthesized probe

<400> SEQUENCE: 1
cctatggctg aaggcggcca gaagcctcac gaagtggtga agttcatgga         50
cgtgtatca                                                     59

<210> SEQ ID NO 2
<211> LENGTH: 59
<212> TYPE: DNA
<213> ORGANISM: Bovine

<400> SEQUENCE: 2
cccatggcag aaggagggca gaaaccccac gaagtggtga agttcatgga         50
tgtctacca                                                     59

<210> SEQ ID NO 3
<211> LENGTH: 270
<212> TYPE: DNA
<213> ORGANISM: Bovine

<400> SEQUENCE: 3
aaccatgaac tttctgctct cttgggtaca ttggagcctt gccttgctgc         50
tctaccttca ccatgccaag tggtcccagg ctgcacccat ggcagaagga         100
gggcagaaac cccacgaagt ggtgaagttc atggatgtct accagcgcag         150
cttctgccgt cccatcgaga ccctggtgga catcttccag gagtacccag         200
atgagattga gttcattttc aagccgtcct gtgtgcccct gatgcggtgc         250
cgcgctgctg taatgacgaa                                         270

<210> SEQ ID NO 4
<211> LENGTH: 89
<212> TYPE: PRT
<213> ORGANISM: Bovine

<400> SEQUENCE: 4

Met Asn Phe Leu Leu Ser Trp Val His Trp Ser Leu Ala Leu Leu
  1               5                  10                  15

Leu Tyr Leu His His Ala Lys Trp Ser Gln Ala Ala Pro Met Ala
                 20                  25                  30

Glu Gly Gly Gln Lys Pro His Glu Val Val Lys Phe Met Asp Val
                 35                  40                  45

Tyr Gln Arg Ser Phe Cys Arg Pro Ile Glu Thr Leu Val Asp Ile
                 50                  55                  60

Phe Gln Glu Tyr Pro Asp Glu Ile Glu Phe Ile Phe Lys Pro Ser
                 65                  70                  75

Cys Val Pro Leu Met Arg Cys Arg Ala Ala Val Met Thr Lys
                 80                  85

<210> SEQ ID NO 5
<211> LENGTH: 39
<212> TYPE: PRT
<213> ORGANISM: Bovine
<220> FEATURE:
<221> NAME/KEY: Unsure
<222> LOCATION: 25
<223> OTHER INFORMATION: X= any amino acid
<220> FEATURE:
```

```
<221> NAME/KEY: Unsure
<222> LOCATION: 33
<223> OTHER INFORMATION: X = any amino acid
<220> FEATURE:
<221> NAME/KEY: Unsure
<222> LOCATION: 35
<223> OTHER INFORMATION: X= any amino acid

<400> SEQUENCE: 5

Ala Pro Met Ala Glu Gly Gly Gln Lys Pro His Glu Val Val Lys
 1               5                  10                  15

Phe Met Asp Val Tyr Gln Arg Ser Phe Xaa Arg Pro Ile Glu Thr
                20                  25                  30

Leu Val Xaa Ile Xaa Gln Glu Tyr Pro
                35

<210> SEQ ID NO 6
<211> LENGTH: 99
<212> TYPE: DNA
<213> ORGANISM: Artificial Sequence
<220> FEATURE:
<223> OTHER INFORMATION: Probe

<400> SEQUENCE: 6
agtagcaagc ttgacgtgtg gcaggcttga gatctggcca tacacttgag            50
tgacaatgac atccactttg cctttctctc cacaggtgtc cactcccag             99

<210> SEQ ID NO 7
<211> LENGTH: 30
<212> TYPE: DNA
<213> ORGANISM: Artificial Sequence
<220> FEATURE:
<223> OTHER INFORMATION: Probe

<400> SEQUENCE: 7
aggctgctgc agttcgacgt gggagtggac                                  30

<210> SEQ ID NO 8
<211> LENGTH: 41
<212> TYPE: DNA
<213> ORGANISM: Artificial Sequence
<220> FEATURE:
<223> OTHER INFORMATION: Factor VIII insertion

<400> SEQUENCE: 8
aagctttcaa aagaaaacac gacactattt tattgctgca g                     41

<210> SEQ ID NO 9
<211> LENGTH: 13
<212> TYPE: PRT
<213> ORGANISM: Artificial Sequence
<220> FEATURE:
<223> OTHER INFORMATION: Factor VIII insertion

<400> SEQUENCE: 9

Ser Phe Gln Lys Lys Thr Arg His Tyr Phe Ile Ala Ala
               5                  10

<210> SEQ ID NO 10
<211> LENGTH: 12
<212> TYPE: DNA
<213> ORGANISM: Artificial sequence
<220> FEATURE:
<223> OTHER INFORMATION: sequence is synthesized

<400> SEQUENCE: 10
```

```
gatcccgtac ta                                                          12

<210> SEQ ID NO 11
<211> LENGTH: 11
<212> TYPE: DNA
<213> ORGANISM: Artificial sequence
<220> FEATURE:
<223> OTHER INFORMATION: sequence is synthesized

<400> SEQUENCE: 11
acttagtacg g                                                           11

<210> SEQ ID NO 12
<211> LENGTH: 12
<212> TYPE: DNA
<213> ORGANISM: Artificial sequence
<220> FEATURE:
<223> OTHER INFORMATION: sequence is synthesized

<400> SEQUENCE: 12
gctcggttcg at                                                          12

<210> SEQ ID NO 13
<211> LENGTH: 18
<212> TYPE: DNA
<213> ORGANISM: Artificial sequence
<220> FEATURE:
<223> OTHER INFORMATION: sequence is synthesized

<400> SEQUENCE: 13
cgatcgaacc gagctgca                                                    18
```

PRODUCTION OF VASCULAR ENDOTHELIAL CELL GROWTH FACTOR AND DNA ENCODING SAME

This is a continuation application filed under 37 CFR 1.53(b) of application Ser. No. 08/978,791 filed Nov. 26, 1997, now abandoned, which is a continuation of Ser. No. 08/749,710 filed Nov. 15, 1996, now abandoned, which is a continuation of Ser. No. 08/459,385 filed Jun. 02, 1995, now abandoned, which is a divisional of Ser. No. 08/306,213 filed Sep. 14, 1994, now abandoned, which is a continuation of Ser. No. 08/047,756 filed on Apr. 15, 1993, now abandoned, which is a continuation of Ser. No. 07/351,117 filed on May 12, 1989, now abandoned, the contents of which are incorporated herein by reference.

BACKGROUND OF THE INVENTION

1. Field of the Invention

This invention relates to a vascular endothelial cell growth factor and to the means and methods for its production in therapeutically significant quantities.

2. Description of the Background Art

Considerable research has been devoted to the morphology and physiology of the secretory cells of the anterior pituitary and pars tuberalis. However, until recently, little was known about the function of the follicular or folliculostellate cells (FC), a morphologically well characterized population of granular cells. The FC are stellate cells that send cytoplasmic processes between secretory cells.

A method for the culture of homogeneous populations of FC is described by Ferrara et al., *Meth. Enz.*, (ed. Conn, P. M.), Vol. 124, pp. 245-253 (Academic Press, New York, 1986). The growth pattern and expression of the dome formation by FC in culture and their ultrastructure have been elucidated. Ferrara et al., *Am J. Physiol.,* 252: E304-312 (1987). In addition, FC have been characterized as ion transport elements, possibly involved in the regulation of ion composition and osmolarity of the interstitial fluid in the adenohypophysial cell cords. Ferrara and Gospodarowitz, *Biochem. Biophys. Res. Comm.*, 157: 1376-1382 (1988). In addition, FC produce the angiogenic sitogen basic fibroblast growth factor (bFGF). Ferrara et al., *Proc. Natl. Acad. Sci., U.S.A.*, 84: 5773-5777 (1987).

The gene encoding bFGF, disclosed in Abraham et al., *EMBO J.* 5: 2523-2529 (1986), does not code for a conventional signal peptide, required for the extracellular transport of proteins according to classical secretory pathways. Walter and Blobel, *J. Cell. Biol.,* 91: 557-561 (1981). Neither does the gene coding for acidic fibroblast growth factor (aFGF), disclosed in Jaye et al., *Science,* 233: 541-544 (1986). Accordingly, the growth factor is not appreciably secreted into the medium [Moscatelli et al., *J. Cell Physiol.,* 129: 273-277 (1986); Klagsburn et al., *Proc. Natl. Acad. Sci.* USA, 83: 2448-2452 (1986)], and responsive cell types are dependent on exogenous bFGF for optimal proliferation in culture, even though they may contain significant intracellular concentrations of the mitogen. Neufeld et al., *Endocrinology,* 121: 597-602 (1987); Schweigerer et al., *Endocrinology,* 120: 796-802 (1987); Schweiger et al., *Exp. Eye Res.,* 46: 71-80 (1988). It has been suggested that bFGF may be incorporated into the basement membrane and be subsequently released in a soluble form only when the matrix is degraded following the action of specific enzymes. Vlodavsky et al., *Proc. Natl. Acad. Sci.* USA, 84: 2282-2286 (1987). Such a mechanism of release suggests a role for the growth factor mostly or exclusively in events that involve degradation of the basement membrane or cell lysis, such as organ remodeling, wound healing, or neoplasia. Folkman and Klagsbrun, *Science,* 235: 442-447 (1987).

Moreover, bFGF and aFGF are both potent mitogens for corneal endothelial cells, lens epithelial cells, BHK-21 fibroblasts, adrenal cortex cells, and keratinocytes, as well as vascular endothelial cells. Gaspodarowitz et al., *Endocrine Reviews,* 8: 95-114 (1987); Baird et al., *Recent Prog. Horm. Res.,* 42: 143-186 (1986).

There is a need for a growth factor that, in contrast to aFGF and bFGF, is not sequestered inside the cell source but rather secreted, with resultant direct access to target cells. Such a growth factor may play a more dynamic role in the physiological regulation of vascular endothelial cell proliferation, either in the cyclical growth of blood vessels that takes place in organs such as the corpus luteum [Bassett, *Am. J. Anat.,* 73: 251-259 (1943)] or in the tonic maintenance of the differentiated state of the endothelium in the vascular tree.

There is also a need for a growth factor that is specific for vascular endothelial cells, in contrast to aFGF and bFGF, which are active on a very broad spectrum of cells. Such specificity may be useful therapeutically for conditions in which a selective action on the vascular endothelial cells, in the absence of excessive connective tissue proliferation, is desirable, such as diabetic ulcers or traumatic vascular injuries.

Although a vascular endothelial cell growth factor meeting the above needs can be isolated and purified from natural sources for subsequent use, the relatively low concentration of the protein in FC and the high cost, both in terms of effort and expense, of recovering in commercial quantities purified growth factor from FC hinder its broad-scale use.

Accordingly, it is an object of the present invention to isolate DNA encoding a vascular endothelial cell growth factor and to produce commercially useful quantities of the protein from a therapeutically acceptable source.

It is a further object to obtain the vascular endothelial cell growth factor in a form unaccompanied by the glycosylation associated with the corresponding native growth factor.

It is an additional object to prepare amino acid sequence and other variants of the vascular endothelial cell growth factor that do not substantially adversely affect the biological activity of the protein.

It is yet another object to produce a vascular endothelial cell growth factor completely free of other naturally occurring (source) proteins.

These and other objects of the invention will be apparent from the specification as a whole.

SUMMARY OF THE INVENTION

The objects of this invention are accomplished by expression of a vascular endothelial cell growth factor in recombinant cell culture, a process that fundamentally comprises providing nucleic acid encoding the growth factor, transforming host cells with the growth factor-encoding nucleic acid, and culturing the cells to express the nucleic acid encoding the growth factor in the host cell culture.

In one specific embodiment, this invention encompasses an isolated nucleic acid sequence comprising a sequence that encodes a vascular endothelial cell growth factor having a molecular weight of about 45,000 daltons under non-reducing conditions and about 23,000 under reducing conditions as measured by SDS-PAGE.

In another aspect the invention provides an isolated DNA sequence comprising a sequence that hybridizes to the DNA sequence: 5'-CCTATGGCTGAAGGCGGCCAGAAGCCT-CACGAAGTGGTGAAGUCATGGACGTGTA TCA-3' (SEQ ID NO:1) when incubated therewith at 42° C. in 20% formamide, 5×SSC, 50 mM sodium phosphate pH 6.8, 0.1% sodium pyrophosphate, 5× Denhardt's solution, and 50 µg/ml salmon sperm DNA, and washed with 2×SSC, 0.1% SDS at 42° C. wherein said sequence contains at least about ten nucleotides.

The DNA sequence may also be characterized as comprising a DNA sequence encoding a vascular endothelial cell growth factor having an amino acid sequence sufficiently duplicative of that of vascular endothelial cell growth factor to allow it to possess the biological property of (a) promoting growth selectively of vascular endothelial cells but not bovine corneal endothelial cells, lens epithelial cells, adrenal cortex cells, BHK-21 fibroblasts, or keratinocytes, or (b) cross-reacting immunologically with an antibody raised against at least one epitope of the corresponding native protein.

In other embodiments, the invention relates to (1) labeled DNA sequences for assay purposes, (2) DNA sequences operably linked to a promoter, (3) expression vectors comprising the DNA sequence described above operably linked to control sequences recognized by a host transformed by the vector, and (4) host cells transformed with the expression vector described above.

Further aspects of the invention are directed to novel forms of the naturally occurring vascular endothelial cell growth factor, including the factor that is unaccompanied by associated native glycosylation, has at least about 80% homology with the amino acid sequence of the mature protein shown in FIG. 2 (SEQ ID NO:4), and possesses one or both of the biological properties of (a) promoting growth selectively of vascular endothelial cells but not bovine corneal endothelial cells, lens epithelial cells, adrenal cortex cells, BHK-21 fibroblasts, or keratinocytes, or (b) cross-reacting immunologically with an antibody raised against at least one epitope of the corresponding native protein. Such a vascular endothelial cell growth factor is generally obtained as a product of expression in heterologous recombinant cell culture. The growth factor in any form as a component of a recombinant cell culture is novel.

In a further embodiment, the invention is directed to a pharmaceutical composition useful for promotion of vascular endothelial cell growth comprising a therapeutically effective amount of the recombinantly produced vascular endothelial cell growth factor in a pharmaceutically acceptable carrier.

Also contemplated herein is a method for treating trauma affecting the vascular endothelium comprising administering to an animal or human suffering from said trauma an effective amount of the above described pharmaceutical composition.

The present invention makes it possible to produce a vascular endothelial cell growth factor and/or derivatives thereof by recombinant techniques, as well as to provide products and methods related to such production.

It is believed that the growth factor prepared by the method described herein is useful for treating conditions in which a selective action on the vascular endothelial cells, in the absence of excessive tissue growth, is important, for example, diabetic ulcers and vascular injuries resulting from trauma such as subcutaneous wounds.

Other uses for the growth factor will be apparent to those skilled in the art.

BRIEF DESCRIPTION OF THE DRAWINGS

FIG. 1 depicts the oligonucleotide probe sequence (SEQ ID NO:1) used to screen human vascular endothelial cell libraries for cDNA clones for the growth factor, as well as the match to the cDNA sequence (SEQ ID NO:2) obtained.

FIG. 2 depicts the partial nucleotide (SEQ ID NO:3) and predicted amino acid sequence (SEQ ID NO:4) of the bovine vascular endothelial cell growth factor herein from the p.vegf.6 clone. Predicted amino acids of the protein are shown below the DNA sequence and are numbered from the first residue of the N-terminus of the protein sequence. Negative amino acid numbers refer to the presumed leader signal sequence or preprotein, while positive numbers refer to the mature protein. The location of the oligonucleotide probe is indicated by underlining.

FIG. 3-1, 3-2, and 3-3 depicts the construction of the starting expression vector pF8CIS used to construct the ultimate expression vector, including using Bam HI-Hind III linkers (SEQ ID Nos: 10 and 11) and Pst1-Clal linkers (SEQ ID Nos: 12 and 13).

DESCRIPTION OF THE PREFERRED EMBODIMENTS

Figures 1, 3:
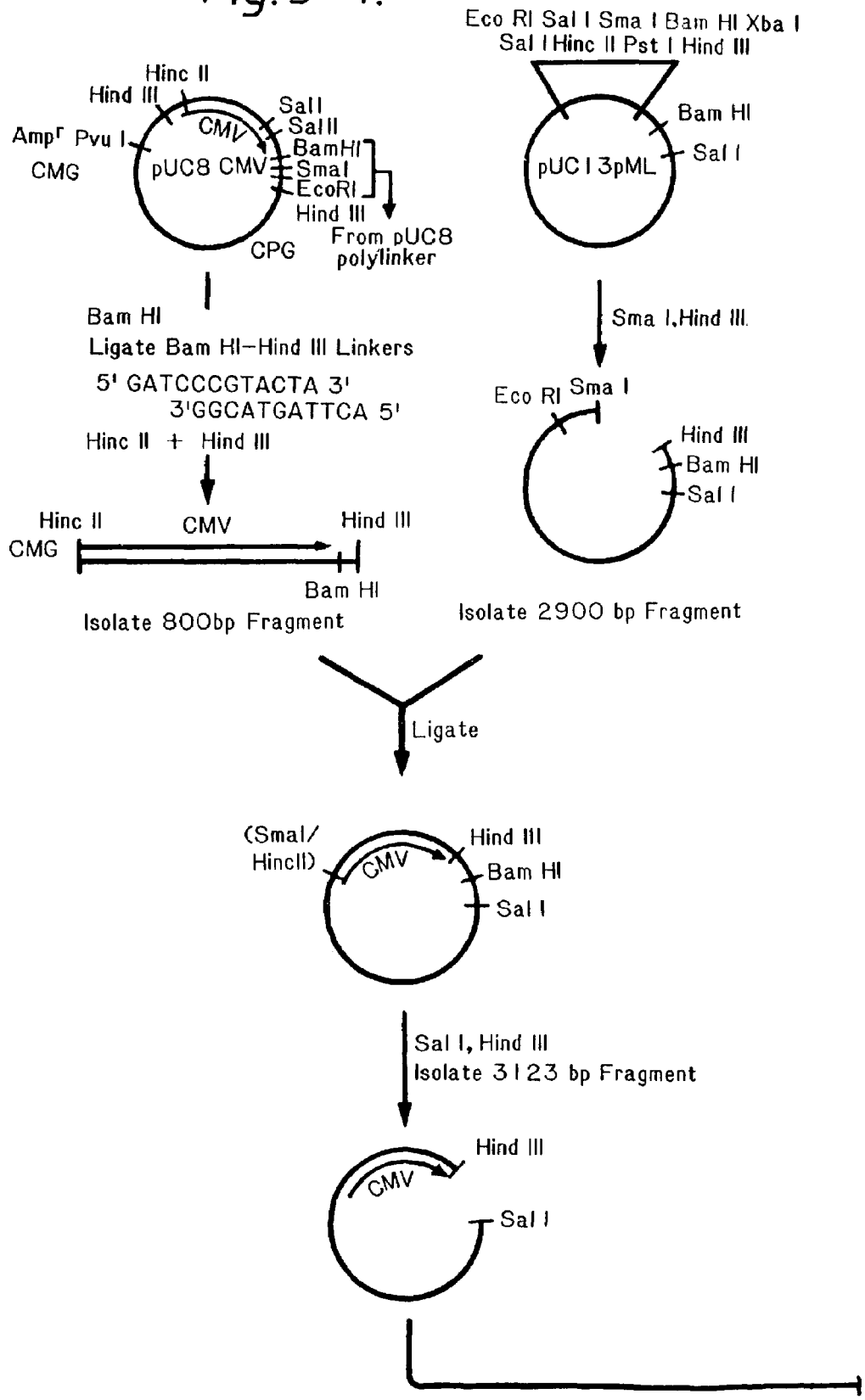
Figures 2, 3:
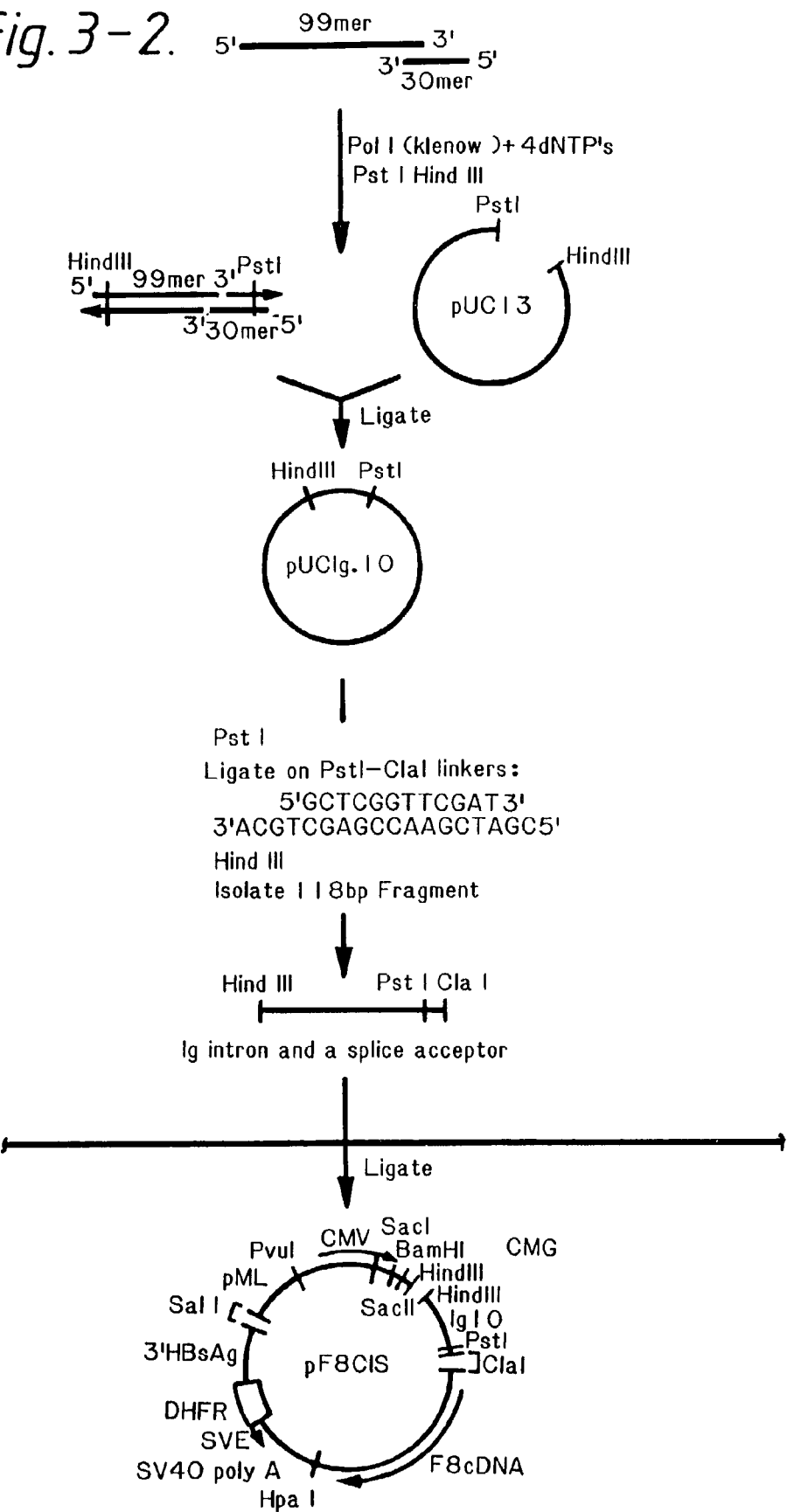
Figure 3:
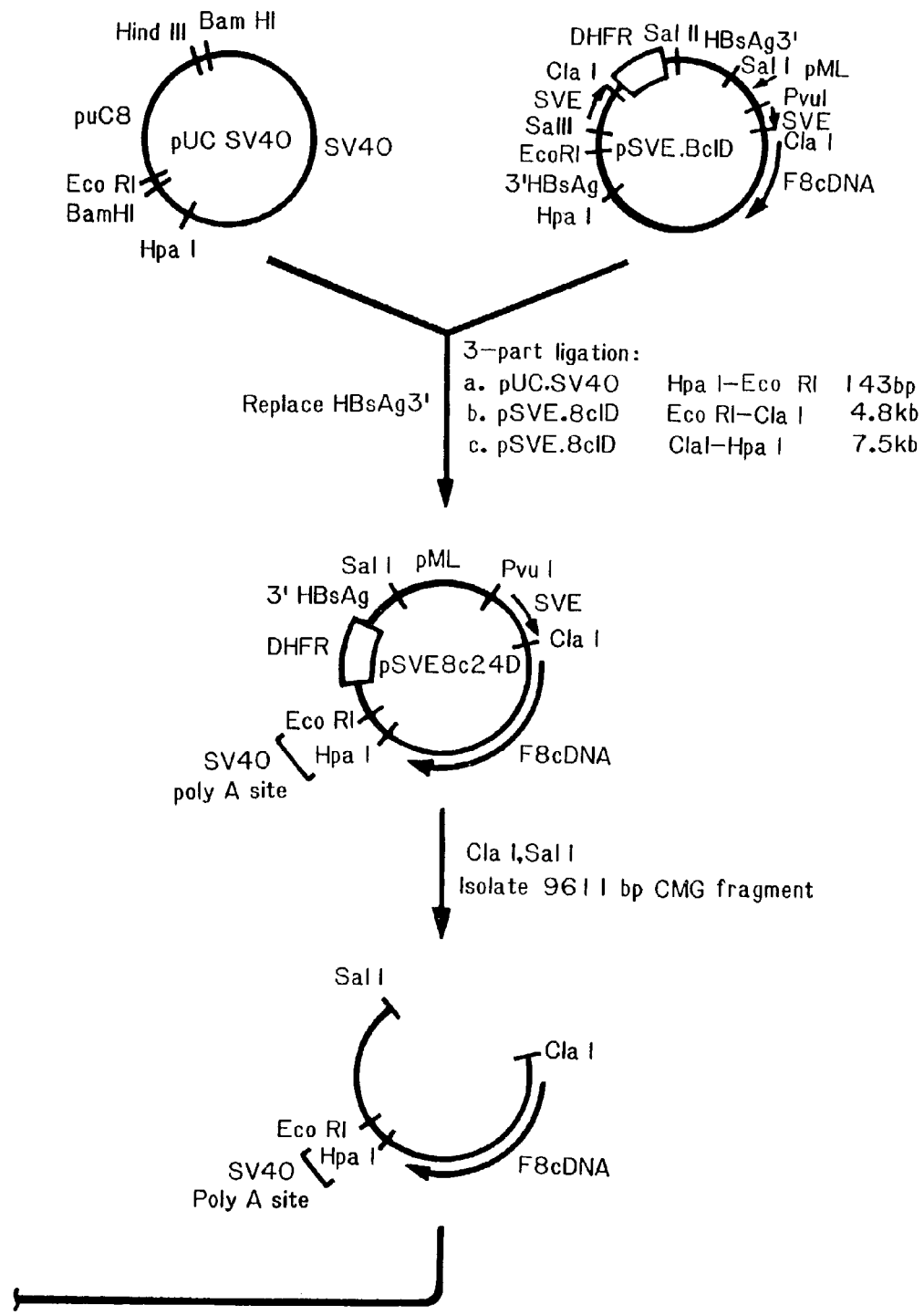

As used herein, "vascular endothelial cell growth factor," or "VEGF," refers to a mammalian growth factor derived originally from bovine pituitary follicular cells having the amino acid sequence of FIG. 2 (SEQ ID NO:4), together with analogues and variants thereof having the biological activity of the corresponding native VEGF. The biological activity of native VEGF is shared by any analogue or variant thereof that is capable of promoting selective growth of vascular endothelial cells but not of bovine corneal endothelial cells, lens epithelial cells, adrenal cortex cells, BHK- 21 fibroblasts, or keratinocytes, or that possesses an immune epitope that is immunologically cross-reactive with an antibody raised against at least one epitope of the corresponding native VEGF.

Analogues or variants are defined as molecules in which the amino acid sequence, glycosylation, or other feature of native VEGF has been modified covalently or noncovalently. Thus, variants may or may not have a molecular weight of approximately 45 kD (as determined by SDS-PAGE carried out in the absence of a reducing agent such as, e.g., β-mercaptoethanol or dithiothreitol). For example, unglycosylcited VEGF having the native mature sequence will have a lower molecular weight on non-reducing SDS-PAGE. Amino acid sequence variants include not only alleles of the FIG. 2 sequence (SEQ ID NO:4), but also predetermined mutations thereof. Generally, amino acid sequence variables have an amino acid sequence with at least about 80% homology, and more typically at least about 90% homology, to that of the native VEGF of FIG. 2 (SEQ ID NO:4). Henceforth, the term VEGF shall mean either the native sequence or a variant form unless otherwise appropriate.

Thus, included within the scope of the present invention is a VEGF having the bovine VEGF amino acid sequence as set forth in FIG. 2 (SEQ ID NO:4), analogous VEGF proteins from other species such as human, equine, porcine, ovine, canine, murine, feline VEGF, and the like, and biologically active amino acid sequence variants of these VEGF molecules, including alleles and in vitro-generated covalent derivatives of VEGF proteins that demonstrate its biological activity.

The expression "trauma affecting the vascular endothelium" refers to trauma, such as injuries, to the blood vessels or heart, including the vascular network of organs, to which an animal or human, preferably a mammal and most preferably a human, is subjected. Examples of such trauma include wounds, incisions, and ulcers, most preferably diabetic ulcers and wounds or lacerations of the blood vessels or heart. Trauma includes conditions caused by internal events as well as those that are imposed by an extrinsic agent such as a pathogen, that can be improved by promotion of vascular endothelial cell growth.

B. MODES OF CARRYING OUT THE INVENTION

1. Modifications of VEGF

Derivatives and amino acid sequence variants of VEGF are useful for their biological activity as it relates to therapeutic utility, as is set forth elsewhere herein, as well as for their ability to bind to anti-VEGF antibodies. The derivatives and variants possessing the latter characteristic are useful in purifying antibodies or, when labeled, as reagents in immunoassays for VEGF, whether or not such derivatives and variants retain their therapeutic biological activity.

a. Covalent Modification

Covalent modifications of a VEGF molecule are included within the scope of this invention. Variant VEGF fragments having up to about 100 residues may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the VEGF to a water-insoluble support matrix or surface for use in the method for purifying anti-VEGF antibodies. Commonly used crosslinking agents include, e.g., 1,1-bis(diazo-acetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79-86 [1983]), acetylation of the N-terminal amine, and, in some instances, amidation of the C-terminal carboxyl group.

b. Mutation(s) in the DNA

Amino acid sequence variants of VEGF can also be prepared by mutations in the DNA. Such variants include, for example, deletions from, or insertions or substitutions of, residues within the amino acid sequence shown in FIG. 2 (SEQ ID NO:4). Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, these variants ordinarily are prepared by site-directed mutagenesis of nucleotides in the DNA encoding the VEGF, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed VEGF variants screened for the optimal combination of desired activity. Techniques for making substitution mutations at predetermined sites in DNA having a known sequence are well known, for example, site-specific mutagenesis.

Preparation of VEGF variants in accordance herewith is preferably achieved by site-specific mutagenesis of DNA that encodes an earlier prepared variant or a nonvariant version of the protein. Site-specific mutagenesis allows the production of VEGF variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA*, 2: 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.*, 153: 3 [1987]) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (USA), 75: 5765 (1978). This primer is then annealed with the single-stranded protein-sequence-containing vector, and subjected to DNA-polymerizing enzymes such as *E coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

c. Types of Mutations

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the mature VEGF sequence) may range generally from about 1 to 10 residues, more preferably 1 to 5. An example of a terminal insertion includes a fusion of a signal sequence, whether heterologous or homologous to the host cell, to the N-terminus of the VEGF molecule to facilitate the secretion of mature VEGF from recombinant hosts.

The third group of variants are those in which at least one amino acid residue in the VEGF molecule, and preferably only one, has been removed and a different residue inserted in its place. Such substitutions preferably are made in accordance with the following Table 1 when it is desired to modulate finely the characteristics of a VEGF molecule.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |

TABLE 1-continued

| Original Residue | Exemplary Substitutions |
| --- | --- |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in VEGF properties will be those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutanyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the VEGF molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native VEGF-encoding nucleic acid, expression of the variant nucleic acid in recombinant cell culture, and, optionally, purification from the cell culture, for example, by immunoaffinity adsorption on a rabbit polyclonal anti-VEGF column (to absorb the variant by binding it to at least one remaining immune epitope).

Since VEGF tends to aggregate into dimers, it is within the scope hereof to provide hetero- and homodimers, wherein one or both subunits are variants. Where both subunits are variants, the changes in amino acid sequence can be the same or different for each subunit chain. Heterodimers are readily produced by cotransforming host cells with DNA encoding both subunits and, if necessary, purifying the desired heterodimer, or by separately synthesizing the subunits, dissociating the subunits (e.g., by treatment with a chaotropic agent such as urea, guanidine hdyrochloride, or the like), mixing the dissociated subunits, and then reassociating the subunits by dialyzing away the chaotropic agent.

The activity of the cell lysate or purified VEGF variant is then screened in a suitable screening assay for the desired characteristic. For example, a change in the immunological character of the VEGF molecule, such as affinity for a given antibody, is measured by a competitive-type immunoassay. Changes in the enhancement or suppression of vascular endothelium growth by the candidate mutants are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily skilled artisan.

3. Recombinant Expression

The VEGF molecule desired may be prepared by any technique, including recombinant methods. Likewise, an isolated DNA is understood herein to mean chemically synthesized DNA, cDNA, chromosomal, or extrachromosomal DNA with or without the 3'- and/or 5'-flanking regions. Preferably, the desired VEGF herein is made by synthesis in recombinant cell culture.

For such synthesis, it is first necessary to secure nucleic acid that encodes a VEGF. DNA encoding a VEGF molecule may be obtained from bovine pituitary follicular cells by (a) preparing a cDNA library from these cells, (b) conducting hybridization analysis with labeled DNA encoding the VEGF or fragments thereof (up to or more than 100 base pairs in length) to detect clones in the library containing homologous sequences, and ©) analyzing the clones by restriction enzyme analysis and nucleic acid sequencing to identify full-length clones. DNA that is capable of hybridizing to a VEGF-encoding DNA under low stringency conditions is useful for identifying DNA encoding VEGF. Both high and low stringency conditions are defined further below. If full-length clones are not present in a cDNA library, then appropriate fragments may be recovered from the various clones using the nucleic acid sequence information disclosed herein for the first time and ligated at restriction sites common to the clones to assemble a full-length clone encoding the VEGF. Alternatively, genomic libraries will provide the desired DNA. The sequence of the DNA encoding VEGF that was ultimately determined is shown in FIG. 2 (SEQ ID NO:3).

Once this DNA has been identified and isolated from the library it is ligated into a replicable vector for further cloning or for expression.

In one example of a recombinant expression system a VEGF-encoding gene is expressed in mammalian cells by transformation with an expression vector comprising DNA encoding the VEGF. It is preferable to transform host cells capable of accomplishing such processing so as to obtain the VEGF in the culture medium or periplasm of the host cell, i.e., obtain a secreted molecule.

a. Useful Host Cells and Vectors

The vectors and methods disclosed herein are suitable for use in host cells over a wide range of prokaryotic and eukaryotic organisms.

In general, of course, prokaryotes are preferred for the initial cloning of DNA sequences and construction of the vectors useful in the invention. For example, *E. coli* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

Prokaryotes may also be used for expression. The aforementioned strains, as well as *E. coli* strains W3110 (F-, lambda-, prototrophic, ATCC No. 27,325), K5772 (ATCC No. 53,635), and SR101, *bacilli* such as *Bacillus subtilis*, and other enterobacteriaceae such as *Salmonella tyhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Chang et al., *Nature*, 375: 615 [1978]; Itakura et al., *Science*, 198: 1056 [1977]; Goeddel et al., *Nature*, 281: 544 [1979]) and a tryptophan (trp) promoter system (Goeddel et al., *Nucleic Acids Res.*, 8: 4057 [1980]; EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell*, 20: 269 [1980]).

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in *Saccharomyces*, the plasmid YRp7, for example (Stinchcomb et al., *Nature*, 282: 39 [1979]; Kingsman et al., *Gene*, 7: 141 [1979]; Tschemper et al., *Gene*, 10: 157 [1980]), is commonly used. This plasmid already contains the trp1 gene that provides a selection marker for a mutant strain of yeast lacking the ability to grow in tryptophan, for example, ATCC No. 44,076 or PEP4-1 (Jones, *Genetics*, 85: 12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; Holland et al., *Biochemistry*, 17: 4900 [1978]), such as enolase, glyceraldehyde-3-phosphate dehydrogenase, hexokinase, pyruvate decarboxylase, phosphofructo-kinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate calls, and propagation of vertebrate cells in culture (tissue culture) has become a routine procedure in recent years [*Tissue Culture*, Academic Press. Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed. along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication [Fiers et al., *Nature*, 273: 113 (1978)]. Smaller or larger SV40 fragments may also be used, provided there is included the approximately 250-bp sequence extending from the HindIII site toward the bglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both VEGF and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci.* (USA) 77: 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

b. Typical Methodology Employable

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments nay be performed using 6 percent polyacrylamide gel described by Goeddel et al., *Nucleic Acids Res.,* 8: 4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.,* 9: 309 (1981) or by the method of Maxam et al., *Methods of Enzymology,* 65: 499 (1980).

After introduction of the DNA into the mammalian cell host and selection in medium for stable transfectants, amplification of DHFR-protein-coding sequences is effected by growing host cell cultures in the presence of approximately 20,000-500,000 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Other techniques employable are described in a section just prior to the examples.

4. Utilities and Formulation

The VEGF molecules herein have a number of therapeutic uses associated with the vascular endothelium. Such uses include the treatment of traumata to the vascular network, in view of the demonstrated rapid promotion by VEGF of the proliferation of vascular endothelial cells that would surround the traumata. Examples of such traumata that could be so treated include, but are not limited to, surgical incisions, particularly those involving the heart, wounds, including lacerations, incisions, and penetrations of blood vessels, and surface ulcers involving the vascular endothelium such as diabetic, haemophiliac, and varicose ulcers. Other physiological conditions that could be improved based on the selective mitogenic character of VEGF are also included herein.

For the traumatic indications referred to above, the VEGF molecule will be formulated and dosed in a fashion consistent with good medical practice taking into account the specific disorder to be treated, the condition of the individual patient, the site of delivery of the VEGF, the method of administration, and other factors known to practitioners. Thus, for purposes herein, the "therapeutically effective amount" of the VEGF is an amount that is effective either to prevent, lessen the worsening of, alleviate, or cure the treated condition, in particular that amount which is sufficient to enhance the growth of vascular endothelium In vivo.

VEGF amino acid sequence variants and derivatives that are immunologically crossreactive with antibodies raised against native VEGF are useful in immunoassays for VEGF as standards, or, when labeled, as competitive reagents.

The VEGF is prepared for storage or administration by mixing VEGF having the desired degree of purity with physiologically acceptable carriers, excipients, or stabilizers. Such materials are non-toxic to recipients at the dosages and concentrations employed. If the VEGF is water soluble, it may be formulated in a buffer such as phosphate or other organic acid salt preferably at a pH of about 7 to 8. If a VEGF variant is only partially soluble in water, it may be prepared as a microemulsion by formulating it with a nonionic surfactant such as Tween, Pluronics, or PEG, e.g., Tween 80, in an amount of 0.04-0.05% (w/v), to increase its solubility.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine,; monosaccharides, disaccharides, and other carbohydrates including cellulose or its derivatives, glucose, mannose, or dextrins; chelating agents such as EDTA; and sugar alcohols such as mannitol or sorbitol.

The VEGF to be used for therapeutic administration must be sterile. Sterility is readily accomplished by filtration through sterile filtration membranes (e.g., 0.2 micron membranes). The VEGF ordinarily will be stored in lyophilized form or as an aqueous solution if it is highly stable to thermal and oxidative denaturation. The pH of the VEGF preparations typically will be about from 6 to 8, although higher or lower pH values may also be appropriate in certain instances. It will be understood that use of certain of the foregoing excipients, carriers, or stabilizers will result in the formation of salts of the VEGF.

If the VEGF is to be used parenterally, therapeutic compositions containing the VEGF generally are placed into a container having a sterile access port, for example, an intravenous solution bag or vial having a stopper pierceable by a hypodermic injection needle.

Generally, where the disorder permits, one should formulate and dose the VEGF for site-specific delivery. This is convenient in the case of wounds and ulcers.

Sustained release formulations nay also be prepared, and include the formation of microcapsular particles and implantable articles. For preparing sustained-release VEGF compositions, the VEGF is preferably incorporated into a biodegradable matrix or microcapsule. A suitable material for this purpose is a polylactide, although other polymers of poly-(α-hydroxycarboxylic acids), such as poly-D-(–)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the condition. This can be determined by routine screening in animal models of the target disorder or, if such models are unavailable, in normal animals.

For examples of sustained release compositions, see U.S. Pat. No. 3,773,919, EP 58,481A, U.S. Pat. No. 3,887,699, EP 158,277A, Canadian Patent No. 1176565, U. Sidman et al., "Biopolymers" 22:547 [1983], and R. Langer et al., "Chem. Tech." 12:98 [1982].

When applied topically, the VEGF is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the VEGF formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as otherified cellulose derivatives, including alkyl celluloses, hydroxyalkyl celluloses, and alkylhydroxyalkyl celluloses, for example, uethylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the VEGF held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400-600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and the VEGF is present in an amount of about 300-1000 μg per ml of gel.

The dosage to be employed is dependent upon the factors described above. As a general proposition, the VEGF is formulated and delivered to the target site or tissue at a dosage capable of establishing in the tissue a VEGF level greater than about 0.1 ng/cc up to a maximum dose that is efficacious but not unduly toxic. This intra-tissue concentration should be maintained if possible by continuous infusion, sustained release, topical application, or injection at empirically determined frequencies.

It is within the scope hereof to combine the VEGF therapy with other novel or conventional therapies (e.g., growth factors such as aFGF, bFGF, PDGF, IGF, NGF, anabolic steroids, EGF or TGF-α) for enhancing the activity of any of the growth factors, including VEGF, in promoting cell proliferation and repair. It is not necessary that such cotreatment drugs be included per se in the compositions of this invention, although this will be convenient where such drugs are proteinaceous. Such admixtures are suitably administered in the same manner and for the same purposes as the VEGF used alone. The useful molar ratio of VEGF to such secondary growth factors is typically 1:0.1-10, with about equimolar amounts being preferred.

In order to simplify the examples and claims, certain frequently occurring methods will be referenced by shorthand phrases.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N. *Proc. Natl. Acad. Sci.* (USA), 69: 2110 (1972) and Mandel et al., *J. Mol. Biol.* 51:154 (1970), is generally used for prokaryotes or other cells that contain substantial cell-wall barriers. For mammalian cells without such cell walls, the calcium phosphate precipitation method of Graham, F. and van der Eb, A., *Virology*, 52: 456-457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al., *J. Bact.*, 130: 946 (1977) and Hsiao, C. L., et al., *Proc. Natl. Acad. Sci.* (USA) 76: 3829 (1979). However, other methods for introducing DNA into cells such as by nuclear injection or by protoplast fusion may also be used.

As used herein, the expression "hybridize under stringent conditions" to describe certain DNA sequences encompassed within the scope of this invention refers to hybridizing under conditions of low ionic strength and high temperature for washing, for example, 0.15 M NaCl/0.015 M sodium citrate/0.1% $NaDodSO_4$ at 50° C., or alternatively the presence of denaturing agents such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate, at 42° C. for hybridization. "Hybridize under low stringency" refers to hybridizing at 42° C. in 20% formamide, 5×SSC, 50 mM sodium phosphate pH 6.8, 0.1% sodium pyrophosphate, 5× Denhardt's solution, and 50 μg/ml salmon sperm DNA, and washing with 2×SSC, 0.1% SDS at 42° C.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning: A Laboratory Manual* (New York: Cold Spring Harbor Laboratory, 1982) pp. 133-134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9:6103-6114 (1981), and D. Goeddel et al., *Nucleic Acids Res,* 8:4057 (1980).

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation, and transfer to nitrocellulose by the method of E. Southern, *J. Mol. Biol.* 98: 503-517 (1975), and hybridization as described by T. Maniatis et al., *Cell* 15: 687-701 (1978).

"Ligation" refers to the process of forming phosphodiester bonds between two double stranded nucleic acid fragments (T. Maniatis et al., 1982, supra, p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Preparation" of DNA from transformants means isolating plasmid DNA from microbial culture. Unless otherwise provided, the alkaline/SDS method of Maniatis et al., 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., *Nucl. Acids Res.,* 14: 5399-5407 [1986]). They are then purified on polyacrylamide gels.

The following examples are intended to illustrate the best mode now known for practicing the invention, but the invention is not to be considered limited thereto.

All literature citations herein are expressly incorporated by reference.

EXAMPLE I

Purification of Native VEGF

Primary cultures of bovine pituitary FC were obtained and established as previously described. Ferrara et al., *Meth. Enzym.*, supra; Ferrara et al., *Am. J. Physiol.*, supra. At confluency, cells were passaged into large-scale tissue culture plates (Applied Sci., San Francisco, Calif.) in the presence of low glucose Dulbecco's modiifed Eagle's medium (DMEM) supplemented with 10% fetal bovine serum, 2 mM glutamine, and antibiotics. Shortly after reaching confluency, the cultures were extensively washed with PBS to remove serum components. The cells were then incubated in a serum-free medium consisting of DMEM plus transferrin (10 g/ml), insulin (5 µg/ml), selenium ($10^{-8}$ M), 2 mM glutamine, and antibiotics. After three or four days, the medium was collected and replaced with fresh serum-free medium. The collected medium was centrifuged (1000× g, 15 min. at 4° C.) and stored at −70° C. The conditioned medium was then collected every three or four days for up to six weeks. The media conditioned by FC was found to stimulate the proliferation rate of low-density microvascular endothelial cells.

Four to six liter batches of conditioned medium (CM) were subjected to ammonium sulfate precipitation. Ammonium sulfate (500 g/L) was added under constant stirring, until the salt was completely in solution. After 8-12 hours in the cold room, the material was centrifuged (20,000×g, 45 min. at 4° C.). The supernatant was discarded and the pellet was resuspended with 10 mM Tris/Cl, pH 7.2, 50 mM NaCl and dialyzed at 4° C. against the same buffer for 8-12 hours. The final volume was 50-60 fold less than the original.

The concentrated CM was applied to a H-S column [Shing et al., *Science*, 223: 1296-1299 (1984)] (10 ml) preequilibrated with 10 mM Tris/Cl, pH 7.2, 50 mM NaCl. The column was then washed with the same buffer until the absorbance at 280 nm was negligible and then eluted stepwise with 10 mM Tris/Cl, pH 7.2 containing 0.15, 0.9, and 3 M NaCl. The flow rate was 1.5 ml/min. Fractions of 1.5 ml were collected and aliquots, diluted with 0.2% gelatin in PBS, were tested for mitogenic activity on endothelial cells. Approximately 90% of the biological activity was eluted in the presence of 0.9 M NaCl. The bioactivity was not affected by heating the fractions at 65° C. for 5 min. and was decreased 25-30% following the exposure to 0.1% TFA (pH2) for two hours. Chromatofocusing using a Mono P column indicated that the p.i. of the growth factor is about 8.5.

The most bioactive H-S fractions (0.9 M NaCl pool) were diluted fourfold with 0.1% trifluoroacetic acid (TFA) in water and applied to a Vydac C4 HPLC column (10×250 mm) preequilibrated in 0.1% TFA/20% acetonitrile. The column was eluted with a linear gradient of acetonitrile (20-45% in 115 min.) at a flow rate of 2 ml/min. The absorbance was monitored at 210 nm. Fractions of 2 ml were diluted in 0.2% gelatin in PBS for assay on endothelial cells. The bioactivity was eluted as a single peak in the presence of about 29% acetonitrile. A silver-stained [Morrissey, *Anal. Biochem.*, 117: 307-310 (1981)] SDS-PAGE gel on the most bioactive fractions revealed the presence of three or four bands.

The most bioactive fractions were pooled, diluted two-fold in 0.1% TFA in water and applied to a second Vydac C4 HPLC column (4.6×250 mm) preequilibrated in 0.1% TFA/ 20% 2-propanol. The column was eluted with a linear gradient of 2-propanol (20-45% in 113 min.). The flow rate was 0.6 ml/min. Aliquots of fractions were diluted for bioassays. The remainder of fractions was dried in a Speed-Vac for SDS/PAGE [Laemmli, *Nature,* 227: 680-685 (1970)] and structural analysis. A single peak of bioactivity corresponding to a distinct peak in the absorption profile was obtained.

The peak fractions from the second reversed phase step displayed a single band on a silver-stained SDS-PAGE, with an apparent molecular weight of about 23,000 under reducing conditions. The intensity of staining of the band was highly correlated to the mitogenic activity across the bioactivity profile. Because previous experiments, using a molecular sieve with a TSK G 3000 SW column suggested a molecular weight in the range of 40-43,000, the possibility that the factor in native conditions was a dimer was considered. This was strongly suggested by the finding that the purified material had an apparent molecular weight of about 45,000 in a silver-stained SDS-PAGE under non-reducing conditions.

Bovine adrenal cortex And brain-derived capillary endothelial cells and bovine adrenal cortex cells are obtained and were maintained as described by Ferrara et al., *Proc. Natl. Acad. Sci.*, supra; Schweigerer et al., *Endocrinology*, supra. Adult or fetal bovine aortic endothelial cells, human umbilical vein endothelial cells, bovine corneal endothelial cells, lens epithelial cells, BHK-21 fibroblasts, and human keratinocytes were cultured and maintained as described by Schweigerer et al., *Exp. Eye Res.*, supra; Jaffe et al., *J. Clin. Inv.*, 51: 46a (1972); Folkman in *Pathobiology of the Endothelial Cell*, Nossel and Vogel, Ed., pp. 79-93 (Academic Press, New York, 1972); D'Amore et al., *Proc. Natl. Acad. Sci.* USA, 78: 3068-3072 (1981); Neufeld et al., *Reg. Pept.*, 13: 293-305 (1986); Pheel and Ham, *In Vitro,* 16: 526-538 (1985). For bioassay, cells were seeded in the presence of their respective growth media at the density of $2 \times 10^4/35$ mm dish or $1 \times 10^4$/well in 12 multiwell plates. Fractions were added to cells in 5 µl/ml aliquots. After 4 or 5 days, cells were dissociated by exposure to trypsin and counted in a Coulter counter.

Figure 5:
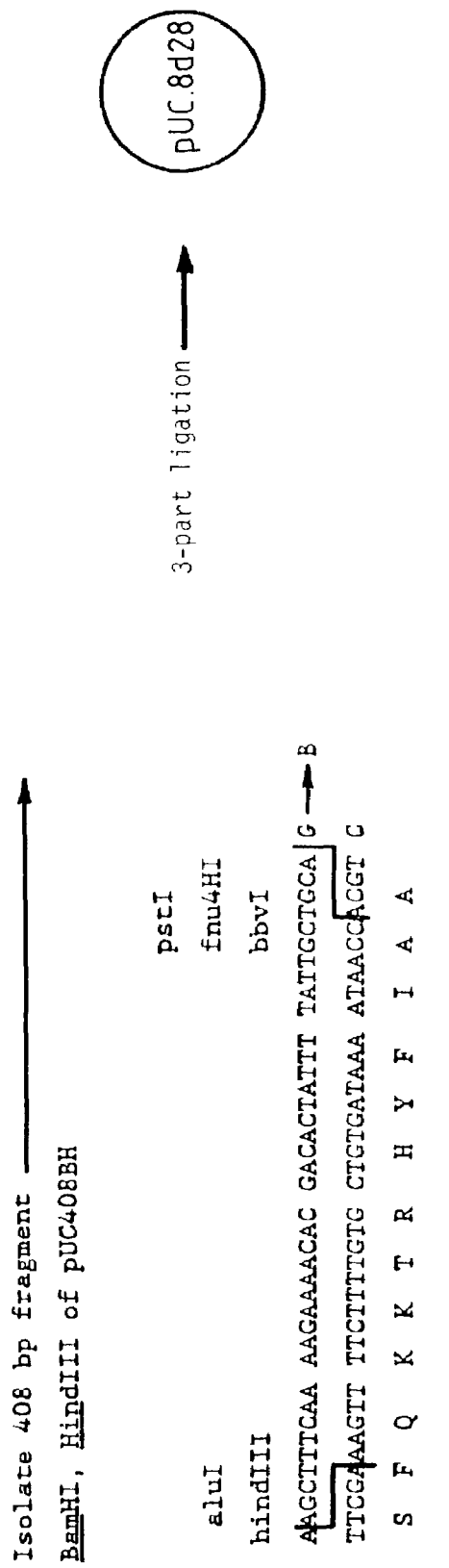
FIG. 5 depicts the construction of the intermediate plasmid pUC.8d28 containing the fusion region of a Factor VIII variant (nucleic acid sequence SEQ ID NO:8 and amino acid sequence SEQ ID NO:9) in a pUC vector.

As shown in FIG. 5, appreciable activity was observed only in cell types of vascular endothelial origin, such as fetal and adult bovine aortic endothelial cells, bovine brain capillary endothelial cells, and human umbilical vein endothelial cells. In contrast, adrenal cortex cells, lens epithelial cells, corneal endothelial cells, BHK-21 fibroblasts, and keratinocytes failed to show any significant mitogenic response.

Approximately 20 pmol of protein from the most bioactive fractions obtained from the second C4 step was applied directly to a gas-phase protein sequenator Model 470A (Applied Biosystems). Edman degradation cycles were carried out by an on-line HPLC column and amino acid derivatives were identified on the HPLC chromatogram. Henzel et al., *J. Chromatograph.*, 404: 41-52 (1987).

The gas-phase microsequencing demonstrated unambiguously a single N-terminal amino acid sequence. The first 39 residues are: Ala-Pro-Met-Ala-Glu-Gly-Gly-Gln-Lys-Pro-His-Glu-Val-Val-Lys-Phe-Met-Asp-Val-Tyr-Gln-(Ar g)-Ser-Phe-X-(Arg)-Pro-Ile-Glu-Thr-Leu-(Val)-X-Ile-X-(Gln)-Glu-Tyr-(Pro) (SEQ ID NO:5), where X represents unknown residues and the parentheses around residues indicate near certainly of the indicated residues, but not complete certainly. This sequence was determined from several N-terminal sequence runs of the intact molecule as well as a sequence run of an HPLC-purified peptide obtained from cyanogen bromide digestion of the intact molecule. A computer search revealed that such sequence does not display significant homology to any previously known protein.

The dose response curve for the purified growth factor revealed a half maximal effect on adrenal cortex-derived endothelial cell proliferation at 100-150 pg/ml and a maximal effect at 1-1.2 ng/ml. These values were derived from protein sequencing and were found to be in good agreement with those obtained by comparing the relative intensities of bands with standards in silver-stained SDS/PAGE.

Table 1 summarizes the steps for the purification of the growth promoting activity and the corresponding yield in bioactivity.

TABLE 1

Summary of Purification of VEGF from 6 L of Conditioned Medium

| Purification Step | Protein (µg) | Maximal Stimulation (ng/ml) | Purification (fold) | Yield (%) |
|---|---|---|---|---|
| C.M* | 190,000 | 2500 | 1 | 100 |
| AS* | 175,000 | 2500 | 1 | 92 |
| H-S* | 13,000 | 250 | 10 | 68 |
| R-P 1** | 25 | 5 | 500 | 6 |
| R-P 2**,# | 4 | 1.2 | 2000 | 4 |

*CM is conditioned medium; AS is ammonium sulfate precipitate; HS is heparin-sepharose; R-P 1 is reversed phase HPLC step 1; and R-P 2 is reversed phase HPLC step 2.
*Protein concentration was determined by BioRad Kit.
**Protein concentration was determined by comparing the relative intensities of bands with standards in silver-stained SDS-PAGE.
Protein concentration was determined by sequencing.

EXAMPLE II

Isolation of VEGF cDNA

Total RNA was extracted [Ullrich et al., *Science*, 196: 1313-1317 (1977)] from bovine pituitary follicular cells [obtained as described by Ferrara et al., *Meth. Enzymol*, supra, and Ferrara et al., *J. Am. Physiol.*, supra] and the polyadenylated mRNA fraction was isolated by oligo(dT)-cellulose chromatography. Aviv et al., *Proc. Natl. Acad. Sci. USA*, 69: 1408-1412 (1972). The cDNA was prepared [Wickens et al., *J. Biol. Chem.*, 253: 2483-2495 (1978)] by priming with $dT_{12-18}$ or a random hexamer $dN_6$. The double-stranded cDNA was synthesized using a cDNA kit from Amersham, and the resulting cDNA was subcloned into EcoRI-cleaved λgt10 as described [Huynh et al., in DNA Cloning Techniques, A Practical Approach, Glover ed. (IRL, Oxford)], except that asymmetric EcoRI linkers [Norris et al., *Gene*, 7: 355-362 (1979)] were used, thus avoiding the need for the EcoRI methylase treatment.

The recombinant phage were plated on *E. ccli* C600 Hfl (Huynh et al., supra) and replica plated onto nitrocellulose filters. Benton et al., *Science*, 196:180-182 (1977). These replica were hybridized with a $^{32}$P-labeled (Taylor et al., *Biochim. Bioohys. Acta*, 442:324-330(1976)) synthetic oligonucleotide probe of the sequence: 5'-CCTATGGCT-GAAGGCGGCCAGAAGCCTCACGAAGTG-GTGAAGTFCATGGACGTGTA TCA-3' (SEQ ID NO:1) at 420° C. in 20% formamide, 5×SSC, 50 mM sodium phosphate pH 6.8, 0.1% sodium pyrophosphate, 5× Denhardt's solution, and 50 µg/ml salmon sperm DNA. and washed in 2×SSC, 0.1% SDS at 4200. FIG. 1 shows a comparison between this probe (SEQ ID NO:1) and the cDNA sequence (SEQ ID NO:2) actually obtained, with the asterisks indicating homologous nucleotides.

One positive clone, designated λ.vegf.6, was identified. This clone, labeled with $^{32}$P, was used as a probe to screen an oligo-dT-primed human placenta cDNA library, and positive clones were observed. When a human pituitary cDNA library was screened with the same labeled clone, no positive clones were detected.

The partial nucleotide sequence of the clone λ.vegf.6 was determined by the dideoxyoligonucleotide chain termination method [Sanger et al., *Proc. Natl. Acad. Sci.* USA, 74: 5463-5467 (1977)] after subcloning into the pRK5 vector. The partial sequence obtained, along with the imputed amino acid sequence, including the signal sequence, is shown in FIG. 2.

Expression of VEGF-Encoding Gene in Mammalian Cells

Figure 8:
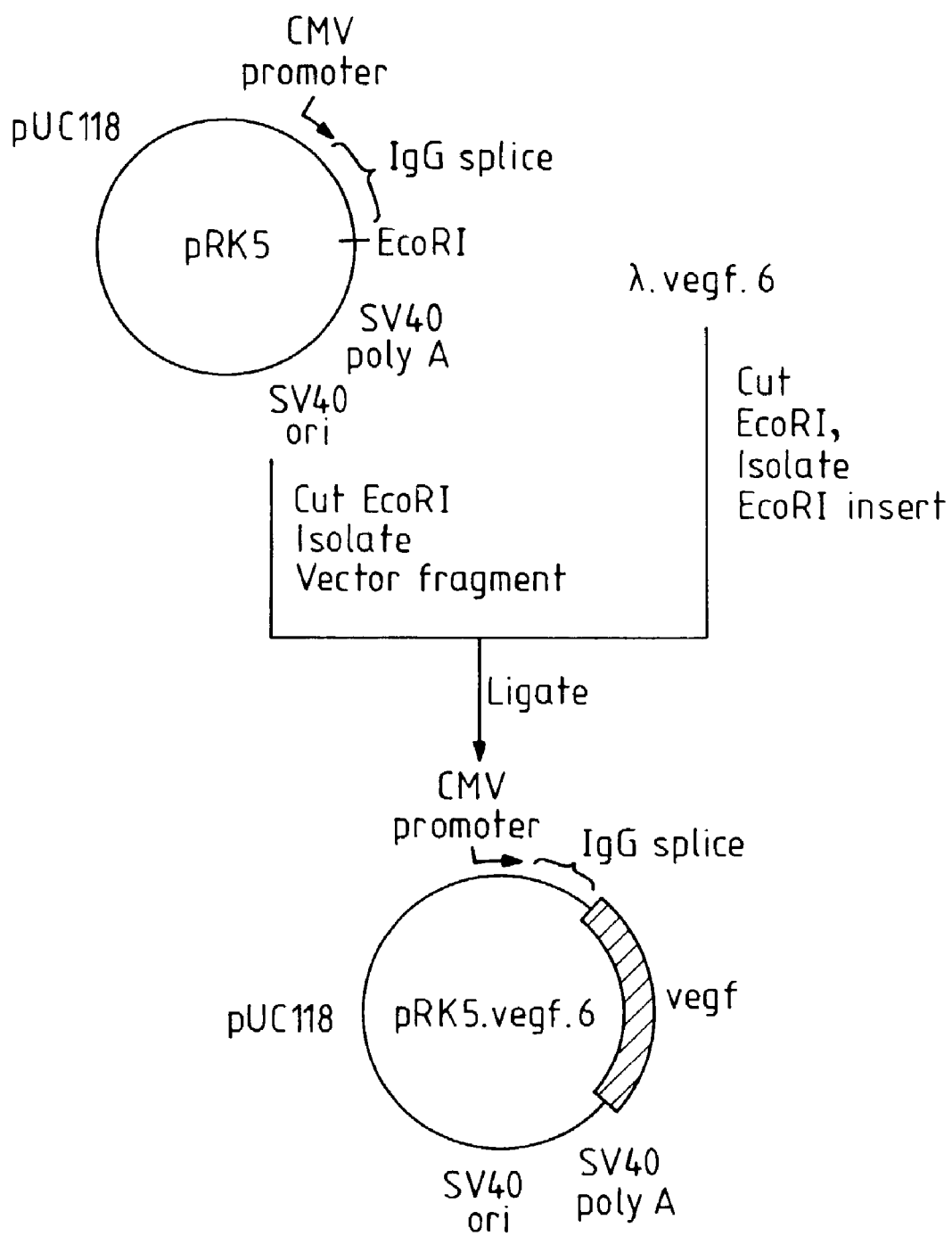
FIG. 8 depicts the construction of the expression vector pRK5.vegf.6 used to transformed mammalian host cells to produce the growth factor.
Figure 9:
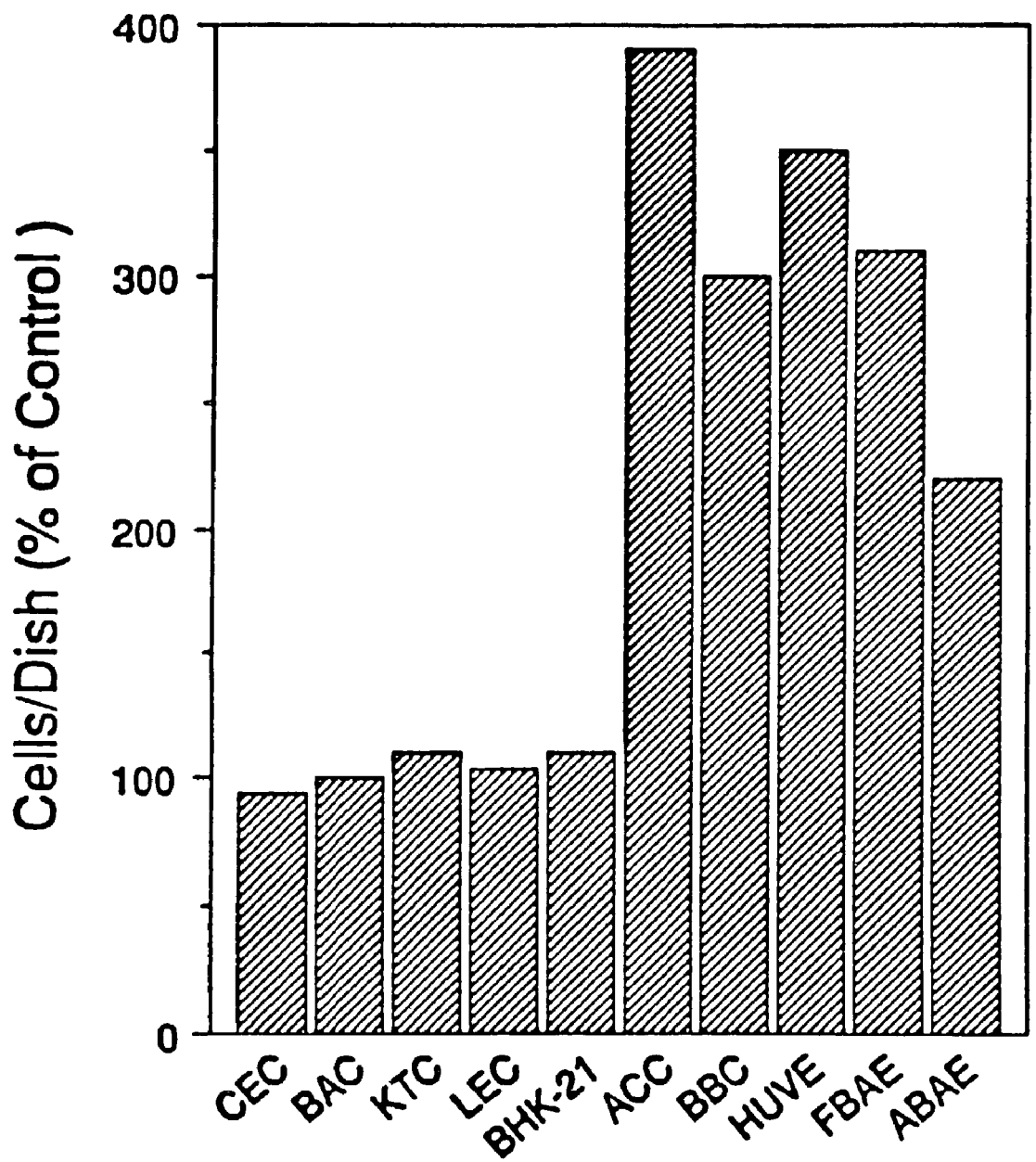
FIG. 9 depicts the effects of the vascular endothelial cell growth factor on the growth of different cell types. CEC, corneal endothelial cells; BAC, bovine adrenal cortex cells; KTC, keratinocytes; LEC, lens epithelial cells; BHK-21, baby hamster kidney cells, clone 21; ACC, adrenal cortex capillary endothelial cells; BBC, bovine brain capillary endothelial cells; HUVE, human umbilical vein endothelial cells; FBAE, feal bovine aortic endothelial cells; ABAE, adult bovine aortic endothelial cells. Cells were seeded in their respective growth media, incubated with a maximal concentration of the growth factor, and counted after 4 or 5 days. The results are expressed as a percent of appropriate control.

The final expression vector, pRK5.vegf.6, was constructed, as shown in FIG. 8, from λ.vegf.6 and pRK5. The construction of pRK5 and pRK5.vegf.6 is described below in detail.

A. Construction of pRK5

A.1. Construction of pF8CIS

The initial three-part construction of the starting plasmid pF8CIS is described below and shown in FIG. 3-1, 3-2, and 3-3.

1) The ampicillin resistance marker and replication origin of the final vector was derived from the starting plasmid pUC13pML. a variant of the plasmid pML (Lusky, M. and Botchen, M., *Nature*, 293: 79 (1981)). pUC13pML was constructed by transferring the polylinker of pUC13 (Vieira, J. and Messing, J., *Gene*, 19:259 (1982) to the EcoRI and HindIII sites of pML. A second starting plasmid pUC8-CMV was the source of the CMV enhancer, promoter and splice donor sequence. pUC8-CMV was constructed by inserting approximately 800 nucleotides for the CMV enhancer, promoter and splice donor sequence into the blunted PstI and Sohl sites of pUC8. Vieira, J. and Messing, J., op. cit. Synthetic BamHI-HindIII linkers (SEQ ID Nos:10 and 11) (commercially available from New England Biolabs) were ligated to the cohesive BamHI end creating a HindIII site. Following this ligation a HindIII-HincII digest was performed. This digest yielded a fragment of approximately 800 bp that contained the CMV enhancer, promoter and splice donor site. Following gel isolation, this 800 bp fragment was ligated to a 2900 bp piece of pUC13pML. The fragment required for the construction of pF8CIS was obtained by digestion of the above intermediate plasmid with SalI and HindIII. This 3123 bp piece contained the resistance marker for ampicillin, the origin of replication from pUC13pML and the control sequences for the CMV, including the enhancer, promoter, and splice donor site.

Figure 4:
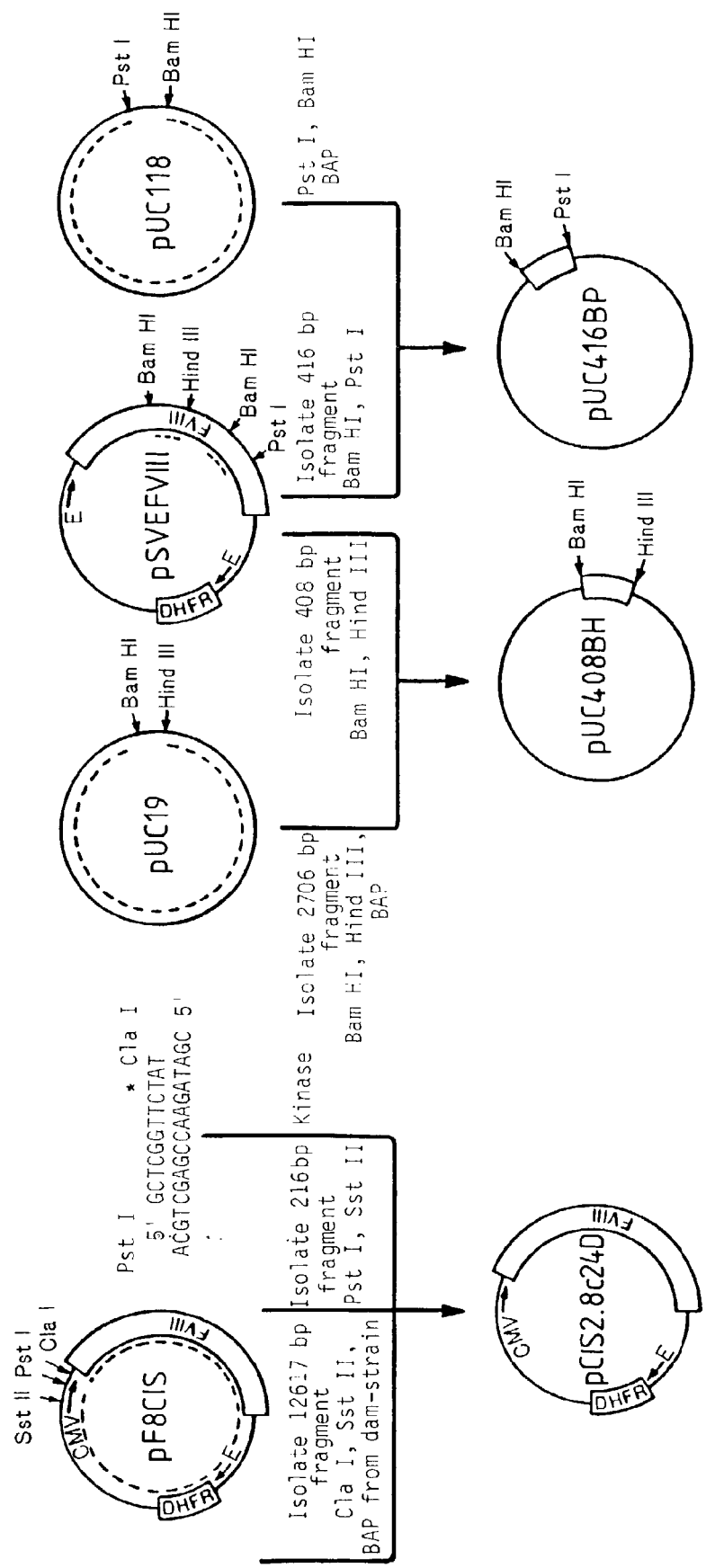
FIG. 4 depicts the construction of the intermediate vector pCIS2.8c24D, including the Pstl-Clal linker (SEQ ID Nos: 12 and 13), for Factor VIII in which the Clal site is not effected by dam methylation. Also shown is the subcloning of 408 and 416 bp fragments of the Factor VIII coding region for construction of a fusion plasmid.

2) The Ig variable region intron and splice acceptor sequence was constructed using a synthetic oligomer as shown in the central portion of FIG. 4. A 99 mer and a 30 mer were chemically synthesized having the following sequence for the lgG intron and splice acceptor site (Bothwell et al., *Nature* 290:65-67 (1981)):

```
  1 5' AGTAGCAAGCTTGACGTGTGGCAGGCTTGA. . .

31    GATCTGGCCATACACTTGAGTGACAATGA. . .

60    CATCCACTTTGCCTTTCTCTCCACAGGT. . .

88    GTCCACTCCCAG 3'
    (SEQ ID NO:6)

1 3' CAGGTGAGGGTGCAGCTTGACGTCGTCGGA 5'
    (SEQ ID NO:7)
```

DNA polymerase I (Klenow fragment) filled in the synthetic piece and created a double-stranded fragment. Wartell, P. M. and W. S. Reznikoff, *Gene,* 2: 307 (1980). This was followed by a double digest of PstI and HindIII (SEQ ID Nos:12 and 13). This synthetic linker was cloned into pUC13 (Veira and Messing, op. cit.) at the PstI and HindIII sites. The clones containing the synthetic oligonucleotide, labeled pUClg.10, was digested with PstI. A ClaI site was added to this fragment by use of a PstI-ClaI linker. Following digestion with HindIII a 118-bp piece containing part of the Ig intron and the Ig variable region splice acceptor was gel isolated.

3) The third part of the construction scheme replaced the hepatitis surface antigen 3' end with the polyadenylation site and transcription termination site of the early region of SV40. A vector, pUC.SV40, containing the SV40 sequences was inserted into pUC8 at the BamHI site described by Vieira and Messing, *op. cit.* pUC.SV40 was then digested with EcoRI and HpaI. A 143 bp fragment containing the SV40 polyadenylation sequence was gel isolated from this digest. Two additional fragments were gel isolated following digestion of pSVE.8c1D. (European Pat. Pub. No. 160,457). The 4.8 kb fragment generated by EcoRI and ClaI digestion contains the SV40-DHFR transcription unit, the origin of replication of pML and the ampicillin resistance marker. The 7.5-kb fragment produced following digestion with ClaI and HpaI contains the cDNA for Factor VIII. A three-part ligation yielded pSVE.8c24D. This intermediate plasmid was digested by ClaI and SalI to give a 9611 bp fragment containing the cDNA for Factor VIII with an SV40 poly A site followed by the SV40 DHFR transcription unit.

The final three-part ligation to yield pF8CIS used: a) the 3123 bp SalI-HindIII fragment containing the origin of replication, the ampicillin resistance marker, and the CKV enhancer, promoter, and splice donor site; b) the 118 bp HindIII-ClaI fragment containing the Ig intron and splice acceptor site; and c) a 9611 bp ClaI-SalI fragment containing the cDNA for Factor VIII, the SV40 polyadenylation site, and the SV40 DHFR transcription unit.

A.2. Construction of pCIS2.8c28D pCIS2.8c28D comprises a 90 kd subunit of Factor VIII joined to a 73 kd subunit of Factor VIII. The 90 kd comprises amino acids 1 through 740 and the 73 kd subunit amino acids 1690 through 2332. This construct was prepared by a three-part ligation of the following fragments: a) the 12617-bp ClaI-SstII fragment of pF8CIS (isolated from a dam-strain and BAP treated); b) the 216-bp SstII-PstI fragment of pF8CIS; and c) a short PstI-ClaI synthetic oligonucleotide that was kinased (see FIG. 5, where an asterisk indicates the changed nucleotide).

FIG. 4 also shows the subcloning of the 408 bp BamHI-HindIII and the 416 bp BamHI-PstI fragments of pSVEFVIIII (European Pat. Publ. No. 160,457) containing the 5' and 3' DNA regions of Factor VIII to be fused to make pCIS2.8c28D.

Figure 6:
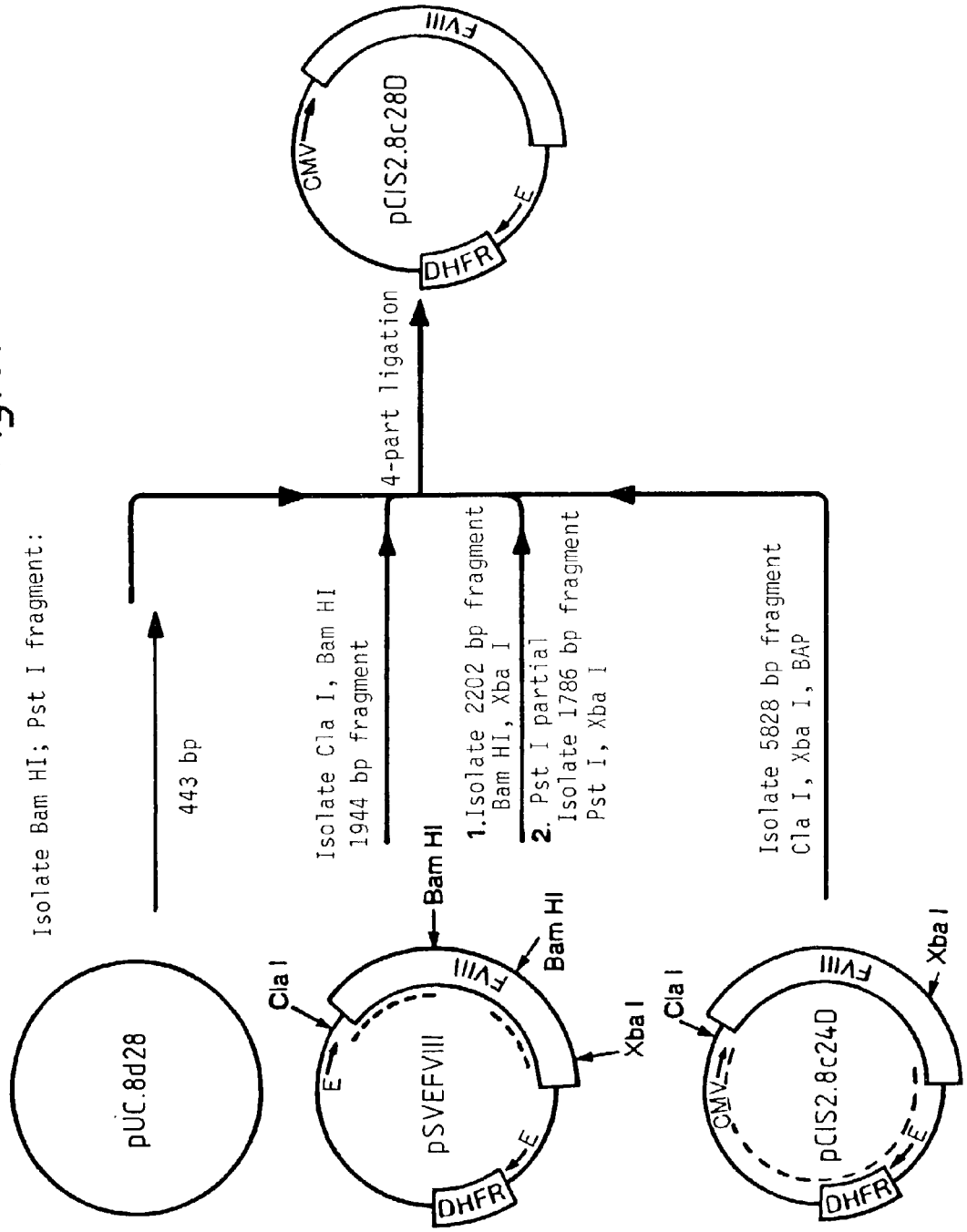
FIG. 6 depicts the construction of the intermediate expression vector encoding a Factor VIII variant protein pCIS2.8c28D.

FIG. 5 shows the three-part ligation used to construct the fusion region of pCIS2.8c28D. Two different fragments, A and B, were cloned into the same pUC118 BamHI-PstI BAP vector. The A fragment was the 408 bp BamHI-HindIII fragment of pUC408BH and the B fragment was a HindIII-PstI oligonucleotide. The double-stranded oligonucleotide is shown in FIG. 6. While complete DNA sequence at the terminal restriction sites is given in FIG. 5, the actual oligonucleotide does not include the bases delineated by the lines at the restriction sites. This oligonucleotide was used without kinasing to prevent its polymerization during ligation.

After ligation of the A and B fragments into the vector as shown in FIG. 5, the expected junction sequences were confirmed by DNA sequencing of the regions encompassed by the nucleotides.

The resulting plasmid, pCIS2.8c28D, was constructed as shown in FIG. 6, with a four-part ligation. The fusion plasmid from FIG. 5 was cut with BamHI and PstI and the 443 bp fragment isolated. The remaining three fragments of the four-part ligation were: 1) 1944 bp ClaI-BamHI of pSVEFVIII (European Pat. Publ. No. 160,457); 2) a 2202 bp BamHI-XbaI fragment of pSVEFVIII, which was further partially digested with PstI and the 1786 bp PstI-XbaI fragment was isolated, and 3) the 5828 bp XbaI-ClaI BAP fragment of pCIS2.8c24D from FIG. 5. The translated DNA sequence of the resultant variant in the exact fusion junction region of pCIS2.8c28D was determined and correlates with the sequence shown in FIG. 5.

A.3. Construction of pRK5

Figure 7:
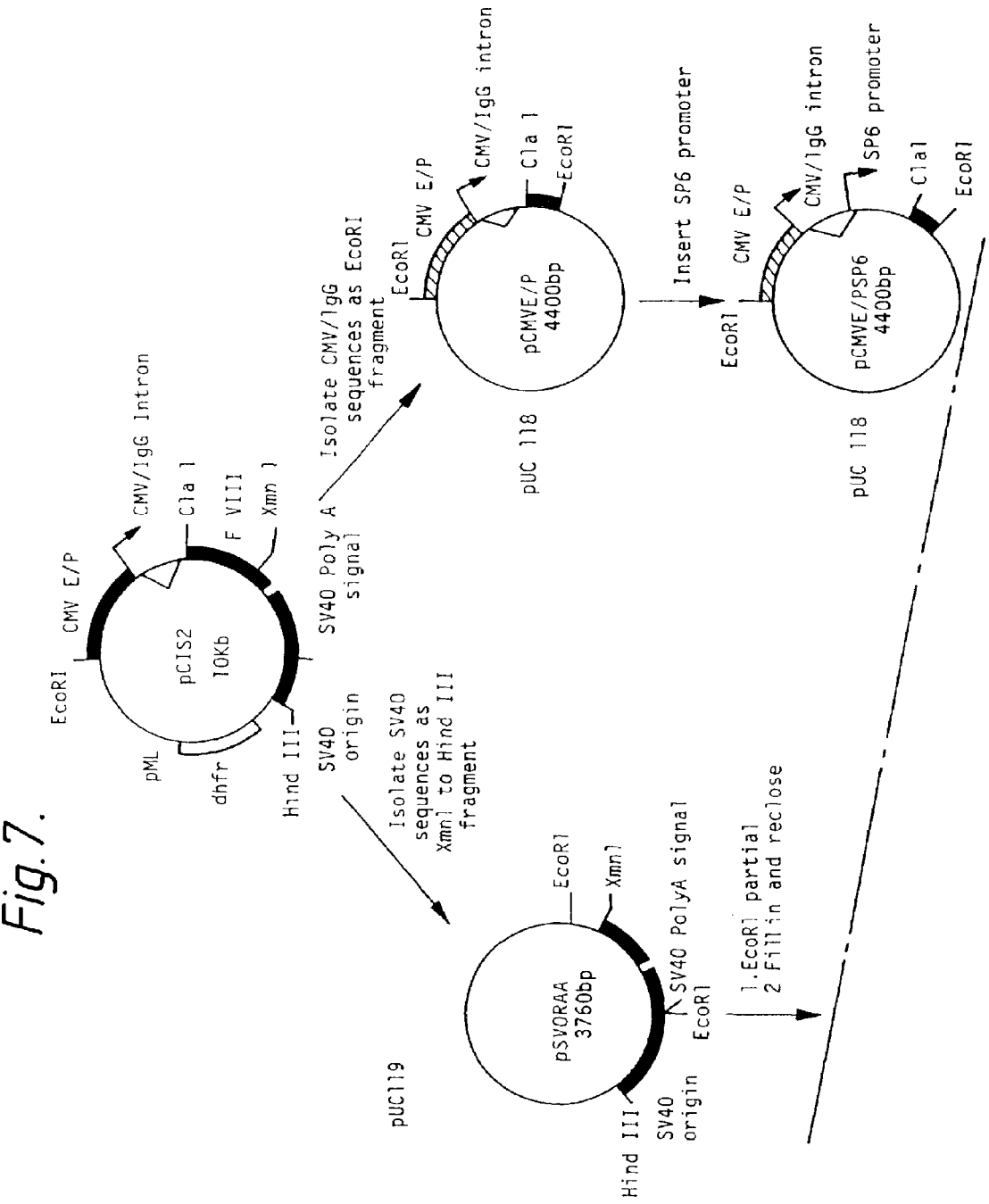
FIG. 7 depicts the construction of the expression vector pRK5 into which the DNA encoding the vascular endothelial cell growth factor was inserted.
Figure 7:
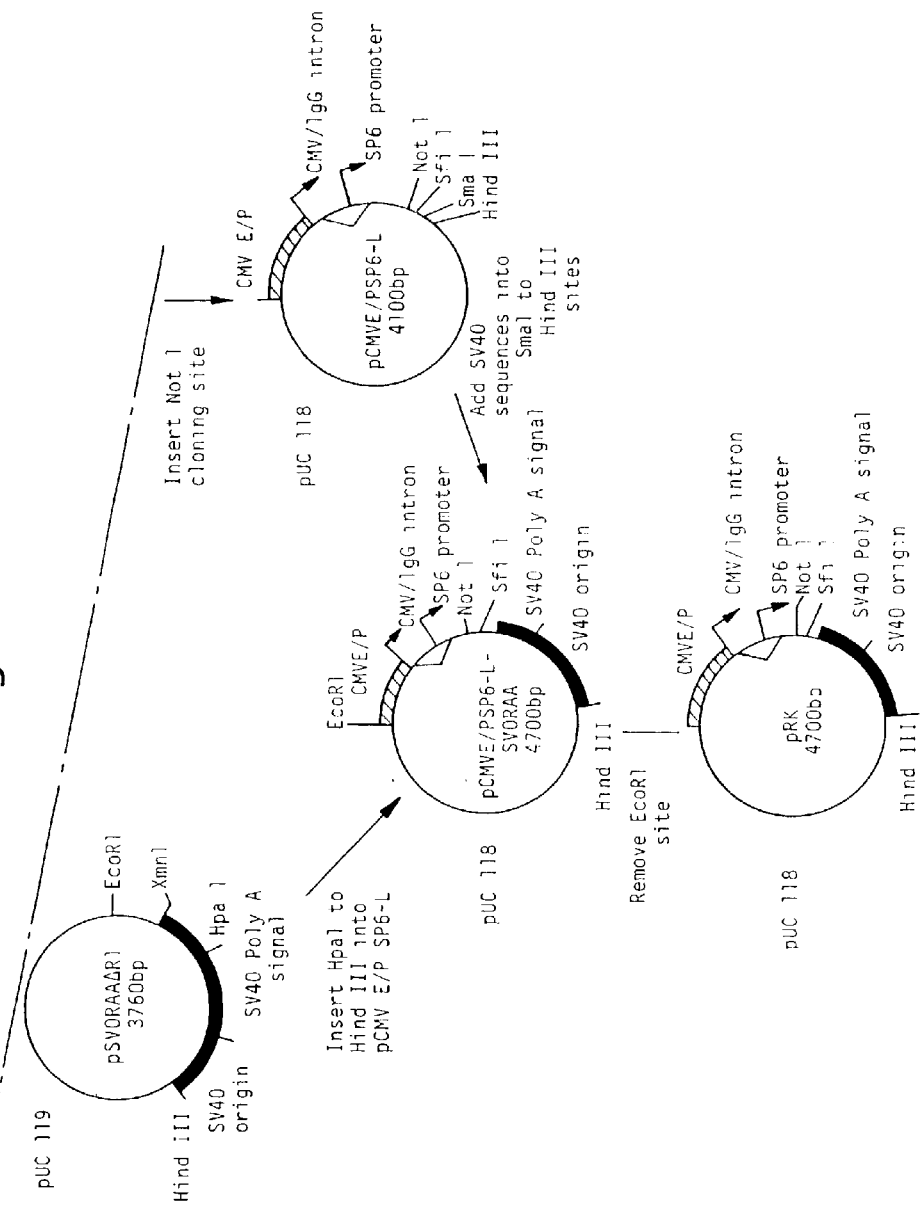

The construction of pRK5 is depicted in FIG. 7. The starting plasmid for construction of pRK5 was pCIS2.8c28D. The base numbers in paragraphs 1 through 6 refer to pCIS2.8c28D with base one of the first T of the EcoRI site preceding the CMV promoter. The cytomegalovirus early promoter and intron and the SV40 origin and polyA signal were placed on separate plasmids.

1. The cytomegalovirus early promoter was cloned as an EcoRI fragment from pCIS2.8c28D (9999-1201) into the EcoRI site of pUC118 described above. Twelve colonies were picked and screened for the orientation in which single-stranded DNA made from pUC118 would allow for the sequencing from the EcoRI site at 1201 to the EcoRI site at 9999. This clone was named pCMVE/P.

2. Single-stranded DNA was made from pCMVE/P in order to insert an SP6 (Green, M R et al., *Cell,* 32: 681-694 [1983]) promoter by site-directed mutagenesis. A synthetic 110 mer that contained the sequences from −69 to +5 of SP6 promoter (see *Nucleic Acids Res.,* 12: 7041 [1984], FIG. 1) were used along with 18-bp fragments on either end of the oligomer corresponding to the CMVE/P sequences. Mutagenesis was done by standard techniques and screened using a labeled 110 mer at high and low stringency. Six potential clones were selected and sequenced. A positive clone was identified and labeled pCMVE/PSP6.

3. The SP6 promoter was checked and shown to be active, for example, by adding SP6 RNA polymerase and checking for RNA of the appropriate size.

4. A Cla-NotI-Sma adapter was synthesized to encompass the location from the ClaI site (912) to the SmaI site of pUC118 in pCMVE/P (step 1) and pCMVE/PSP6 (step 2). This adapter was ligated into the ClaI-SmaI site of pUC118 and screened for the correct clones. The linker was sequenced in both and clones were labeled pCMVE/PSP6-L and pCMVE/P-L.

5. pCMVE/PSP6-L was cut with SmaI (at linker/pUC118 junction) and HindIII (in pUC118). A HpaI (5573)-to-HindIII (6136) fragment from pSVORAAΔRI 11, described below, was inserted into SmaI-HindIII of pCMVE/PSP6-L. This ligation was screened and a clone was isolated and named pCMVE/PSP6-L-SVORAAΔRI.

a) The SV40 origin and polyA signal was isolated as the XmnI (5475)-HindIII (6136) fragment from pCIS2.8c28D and cloned into the HindIII to SmaI sites of pUC119 (described in Vieira and Messing, *op. cit.*). This clone was named pSVORAA.

b) The EcoRI site at 5716 was removed by partial digestion with EcoRI and filling in with Klenow. The colonies obtained from self-ligation after fill-in were screened and the correct clone was isolated and named pSVORAAΔRI 11. The deleted EcoRI site was checked by sequencing and shown to be correct.

c) The HpaI (5573) to HindIII (6136) fragment of pSVORAAΔRI 11 was isolated and inserted into pCMVE/PSP6-L (see 4 above).

6. pCMVE/PSP6-L-SVOrAAΔRI (step 5) was cut with EcoRI at 9999, blunted and self-ligated. A clone without an EcoRI site was identified and named pRK.

7. pRK was cut with SmaI and BamHI. This was filled in with Klenow and relegated. The colonies were screened. A positive clone was identified and named pRKΔBam/Sma3.

8. The HindIII site of pRKDBam/Sma3 was converted to a HpaI site using a converter. (A converter is a piece of DNA used to change one restriction site to another. In this case one end would be complementary to a HindIII sticky end and the other end would have a recognition site for HpaI.) A positive clone was identified and named pRKΔBam/Sma, HIII-HpaI 1.

9. pRKΔBam/Sma, HIII-HpaI 1 was cut with PstI and NotI and an EcoRI-HindIII linker and HindIII-EcoRI linker were ligated in. Clones for each linker were found. However, it was also determined that too many of the HpaI converters had gone in (two or more converters generate a PvuII site). Therefore, these clones had to be cut with HpaI and self-ligated.

10. RI-HIII clone 3 and HIII-RI clone 5 were cut with HpaI, diluted, and self-ligated. Positives were identified. The RI-HIII clone was named pRK5.

B. Construction of pRK5.vegf.6

FIG. 8 depicts the construction of pRK5.vegf.6. The clone λ.vegf.6, having EcoRI insert, was ligated into the vector fragment of pRK5 obtained by digestion of pRK5 with EcoRi and isolation of the large fragment. The two-part ligation of these fragments yielded the expression vector, pRK5.vegf.6, which was screened for the correct orientation of the VEGF-encoding sequence with respect to the promoter.

C. Expression of VEGF-Encoding Gene

Human embryonic kidney cells transformed with adenovirus E1a dn E1b (293s) have been described by Graham et al., *J. Gen. Virol.,* 36: 59-73 (1977). These cells were transfected with the above-described expression vector pRK5.vegf.6 by the calcium phosphate method of Gorman, in *DNA Cloning,* D. M. Glover, ed. (IRC Press, Oxford, 1985), vol. 2, pp. 143-190. After 24 hours, the cells were changed to a serum-free medium for an additional 48-hour incubation. This serum-free medium was then harvested and the supernatant therefrom assayed for VEGF activity.

EXAMPLE III

Assay for VEGF Activity

The supernatant from the transformed cells produced in Example IIC above is tested for bioactivity of VEGF using the same cell lines as used in the protein purification procedure described above. Thus, fractions of the supernatants are added in 5 µl/ml aliquots to the various cell types seeded in the presence of their respective growth media in multiwell plates. After four or five days, the cells are dissociated by exposure to trypsin and counted in a Coulter counter. Cell supernatants that contain VEGF are efficacious in promoting the proliferation of fetal and adult bovine aortic endothelial cells, bovine brain capillary endothelial cells, and human umbilical vein endothelial cells, but do not support the growth of adrenal cortex cells, lens epithelial cells, corneal endothelial cells, BHK-21 fibroblasts, and keratinocytes.

SUMMARY

In summary, the identification of the partial nucleic acid sequence encoding VEGF has been determined, with VEGF being a dimer composed of two subunits of the same apparent molecular weight (each being 23,000). The growth factor in pure form was able to stimulate the proliferation of vascular endothelial cells at concentrations between about 25 and 101.2 ng/ml. These values, assuming a molecular weight of 45,000, correspond respectively to 0.55 pM and 22-26 pM, which are in the same range as those obtained with bFGF. Gospodarowicz et al., *Endocrine Reviews,* supra. VEGF appears to differ from a recently purified [Miyazono et al., *J. Biol. Chem.,* 262:4098-4113 (1987)] and cloned (Ishikawa et al., *Nature,* 38: 557-561 (1989)) endothelial cell growth factor isolated from human platelets (PD-ECGF). Although PD-ECGF and the VEGF have the same molecular mass, they differ in their N-terminal sequence, secondary structure, and biological potency. Unlike VEGF, PD-ECGF is constituted by a single polypeptide chain and also appears to be about 10 fold less potent in promoting endothelial cell growth. Also, PD-ECGF does not bind to heparin-sepharose and is an acidic protein, while VEGF binds to heparin and has a basic p.i.

The ability of VEGF to bind heparin may have implications as to its In vivo function and regulation. Heparin sulfates are fundamental components of the extracellular matrix and have been proposed to play a crucial role in determining contact between target cells and heparin-binding growth factors.

The presence of VEGF in pituitary FC strongly suggests a role for these cells in the development, organization, and maintenance of a differentiated stage of the complex microvasculature of the adenohypophysis.

It is presently unknown whether VEGF is expressed in organs other than the pituitary gland. However, considering the fundamental role of vascular endothelial cell growth and angiogenesis in a great variety of normal and pathological proliferations, the distribution of VEGF is likely to be more widespread.

What is claimed is:

1. An isolated DNA sequence comprising a sequence that hybridizes to the DNA sequence of FIG. 2 (SEQ ID NO:3) when incubated therewith at 42° C. in 20% formamide, 5×SSC, 50 mM sodium phosphate pH 6.8, 0.1% sodium pyrophosphate, 5× Denhardt's solution, and 50 µg/ml salmon sperm DNA, and washed with 2×SSC, 0.1% SDS at 42° C., wherein said isolated sequence contains at least about thirty nucleotides.

2. The nucleic acid sequence of claim 1 further comprising a promoter operably linked to said nucleic acid sequence.

3. An expression vector comprising the nucleic acid sequence of claim 1 operably linked to control sequences recognized by a host transformed by the vector.

4. A host cell transformed with the expression vector of claim 3.

5. The host cell of claim 4 wherein the cell is eukaryotic.

6. The host cell of claim 4 wherein the cell is prokaryotic.

* * * * *